(12) United States Patent
Haun et al.

(10) Patent No.: US 12,292,046 B2
(45) Date of Patent: May 6, 2025

(54) MICROFLUIDIC FILTER DEVICE AND METHOD FOR DISSOCIATION OF TISSUE AND CELL AGGREGATES AND ENRICHMENT OF SINGLE CELLS

(71) Applicant: THE REGENTS OF THE UNIVERSITY OF CALIFORNIA

(72) Inventors: Jered Haun, Irvine, CA (US); Xiaolong Qiu, Irvine, CA (US); Marissa Noelani Pennell, Rocklin, CA (US); Elliott E. Hui, South Pasadena, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1031 days.

(21) Appl. No.: 17/058,634

(22) PCT Filed: May 29, 2019

(86) PCT No.: PCT/US2019/034470
§ 371 (c)(1),
(2) Date: Nov. 24, 2020

(87) PCT Pub. No.: WO2019/232100
PCT Pub. Date: Dec. 5, 2019

(65) Prior Publication Data
US 2021/0205810 A1    Jul. 8, 2021

Related U.S. Application Data

(60) Provisional application No. 62/678,171, filed on May 30, 2018.

(51) Int. Cl.
*B01D 63/00*    (2006.01)
*B01D 63/08*    (2006.01)
(Continued)

(52) U.S. Cl.
CPC ............ *F04B 43/04* (2013.01); *B01D 63/005* (2013.01); *B01D 63/088* (2013.01);
(Continued)

(58) Field of Classification Search
CPC ..... F04B 43/04; B01D 63/005; B01D 63/088; B01D 2319/025; B01D 2325/0283;
(Continued)

(56) References Cited

U.S. PATENT DOCUMENTS 9,580,678 B2    5/2017  Haun et al.
10,722,540 B1   7/2020  Haun et al.
(Continued)

FOREIGN PATENT DOCUMENTS

EP       3070160 A1      9/2016
JP      2007-501633      2/2007
(Continued)

OTHER PUBLICATIONS

Response to Notice of Rejection dated Jul. 18, 2023 for Japanese Patent Application No. 2020-566610, English Translation for Amended Claims only (10 pages).
(Continued)

*Primary Examiner* — Liban M Hassan
(74) *Attorney, Agent, or Firm* — VISTA IP LAW GROUP LLP

(57) ABSTRACT

A microfluidic tissue dissociation and filtration device simultaneously filters large tissue fragments and dissociates smaller aggregates into single cells, thereby improving single cell yield and purity. The device includes an inlet coupled to a first microfluidic channel at an upstream location and a first outlet at a downstream location. A first filter membrane is interposed between the first microfluidic channel and a second microfluidic channel, wherein the second microfluidic channel is in fluidic communication
(Continued)

with the first microfluidic channel via the first filter membrane. The first filter membrane operates under a tangential flow format. A second outlet is coupled to a downstream location of the second microfluidic channel and includes a second filter membrane interposed between the second outlet and the second microfluidic channel. The dual membrane device increased single cell numbers by at least 3-fold for different tissue types.

10 Claims, 13 Drawing Sheets

(51) Int. Cl.
    *B01L 3/00*            (2006.01)
    *F04B 43/04*         (2006.01)

(52) U.S. Cl.
    CPC .. *B01L 3/502761* (2013.01); *B01D 2319/025* (2013.01); *B01D 2325/0283* (2022.08); *B01L 2200/027* (2013.01); *B01L 2200/0652* (2013.01); *B01L 2300/0681* (2013.01); *B01L 2300/0816* (2013.01); *B01L 2300/0864* (2013.01)

(58) Field of Classification Search
    CPC ............... B01D 2325/02; B01D 69/02; B01L 3/502761; B01L 2200/027; B01L 2200/0652; B01L 2300/0681; B01L 2300/0816; B01L 2300/0864; B01L 3/502753; C12M 23/16; C12M 29/04; G01N 2001/4088; G01N 1/4077
    See application file for complete search history.

(56) References Cited

U.S. PATENT DOCUMENTS

| | | | |
|---|---|---|---|
| 2004/0051154 A1* | 3/2004 | Yamakawa | B01L 3/502753 257/414 |
| 2004/0259177 A1 | 12/2004 | Lowery et al. | |
| 2011/0008397 A1 | 1/2011 | Cohen | |
| 2011/0151479 A1* | 6/2011 | Stevens | G01N 33/54366 435/7.1 |
| 2014/0377866 A1 | 12/2014 | Haun et al. | |
| 2015/0118728 A1* | 4/2015 | Rahman | B01L 3/502753 422/534 |
| 2015/0165346 A1 | 6/2015 | Puleo et al. | |
| 2016/0310940 A1* | 10/2016 | Rajagopal | C12Q 1/10 |
| 2017/0131187 A1 | 5/2017 | Haun et al. | |
| 2017/0145053 A1 | 5/2017 | Brellisford et al. | |
| 2018/0015423 A1 | 1/2018 | Kim et al. | |
| 2018/0361382 A1 | 12/2018 | Zobi et al. | |
| 2019/0070605 A1 | 3/2019 | Haun et al. | |

FOREIGN PATENT DOCUMENTS

| | | |
|---|---|---|
| JP | 2012-501245 A | 1/2012 |
| JP | 2014-113064 | 6/2014 |
| JP | 2015-012839 A | 1/2015 |
| JP | 2016-052300 | 4/2016 |
| JP | 2016-195589 | 11/2016 |
| KR | 20120042531 A | 5/2012 |
| WO | WO 2004/101753 A2 | 11/2004 |
| WO | WO 2010/027955 A2 | 3/2010 |
| WO | 2018/003476 A1 | 1/2018 |
| WO | WO 2018/189040 | 10/2018 |

OTHER PUBLICATIONS

The extended European search report dated Jun. 28, 2021, for European Patent Application No. 19811784.8-1004, Applicant: The Regents of the University of California, (9 pages).
Communication pursuant to Rules 70(2) and 70a(2) EPC dated Jul. 15, 2021, for European Patent Application No. 19811784.8-1004, Applicant: The Regents of the University of California, (1 page).
Hattersley, S.M. et al., Development of a microfluidic device for the maintenance and interrogation of viable tissue biopsies, Lab Chip, 2008, 8, 1842-1846.
Zheng, S. et al., Membrane microfilter device for selective capture, electrolysis and genomic analysis of human circulating tumor cells, Journal of Chromatography A, 1162 (2007) 154-161.
Fan, X. et al., A microfluidic chip integrated with a high-density PDMS-based microfiltration membrane for rapid isolation and detection of circulating tumor cells, Biosensors and Bioelectronics 71 (2015) 380-386.
Response to the extended European search report dated Apr. 25, 2022, for European Patent Application No. 19811784.8-1004, Applicant: The Regents of the University of California, (63 pages).
PCT International Search Report and Written Opinion for PCT/US2019/034470, Applicant: The Regents of the University of California, dated Aug. 19, 2019 (8 pages).
Sarioglu, A.F. et al., A microfluidic device for label-free, physical capture of circulating tumor cell-clusters, Nat Methods. Jul. 2015 ; 12(7): 685-691. doi:10.1038/nmeth.3404.
Coumans, F.A.W. et al., Filtration Parameters Influencing Circulating Tumor Cell Enrichment from Whole Blood, PLoS ONE 8(4): e61774. doi:10.1371/journal.pone.0061774 (Apr. 2013).
Didar, T. F. etal., Separation of rare oligodendrocyte progenitor cells from brain using a high-throughput multilayer thermoplastic-based microfluidic device, Biomaterials 34 (2013) 5588e5593.
Krebs, M.G. et al., Analysis of Circulating Tumor Cells in Patients with Non-small Cell Lung Cancer Using Epithelial Marker-Dependent and -Independent Approaches, Journal of Thoracic Oncology | vol. 7, No. 2, Feb. 2012.
Lin, C-H et al., Single-Cell Enzyme-Free Dissociation of Neurospheres Using a Microfluidic Chip, dx.doi.org/10.1021/402724b, Anal. Chem. 2013, 85, 11920-11928.
Zhout, M-D. et al., Separable Bilayer Microfiltration Device for Viable Label-free Enrichment of Circulating Tumour Cells, Scientific Reports, (2014) 4:7392, DOI: 10.1038/srep07392.
Qiu, X. et al., Microfluidic device for mechanical dissociation of cancer cell aggregates into single cells, Lab Chip. Jan. 7, 2015; 15(1): 339-350. doi:10.1039/c4lc01126k.
Qiu, X. et al., Microfluidic channel optimization to improve hydrodynamic dissociation of cell aggregates and tissue, Scientific Reports, (2018) 8:2774, DOI:10.1038/s41598-018-20931-y.
Qiu, X. et al., Microfluidic device for rapid digestion of tissues into cellular suspensions, Lab Chip. Sep. 26, 2017; 17(19): 3300-3309. doi: 10.1039/c7lc00575j.
Vona, G. et al., Isolation by Size of Epithelial Tumor Cells A New Method for the Immunomorphological and Molecular Characterization of Circulating Tumor Cells, American Journal of Pathology, vol. 156, No. 1, Jan. 2000.
Wallman, L. et al., Biogrid—a microfluidic device for large-scale enzyme-free dissociation of stem cell aggregates, Lab Chip, 2011, 11, 3241.
Kang, Y-T. et al., Label-free Rapid Viable Enrichment of Circulating Tumor Cell by Photosensitive Polymer-based Microfilter Device, Theranostics, 2017; 7(13): 3179-3191. doi: 10.7150/thno. 19686.
Response to Office Action dated Nov. 29, 2023 for Japanese Patent Application No. 2020-566610; English Translations for Claims only; (7 pages).
Notice of Allowance dated Feb. 1, 2024, for Japanese Patent Application No. 2020-566610; (8 pages).
Communication under Rule 71(3) EPC dated Dec. 18, 2023, for European Patent Application No. 19811784.8-1004, (84 pages).
Communication under Rule 71(3) EPC dated Dec. 8, 2023, for European Patent Application No. 19811784.8-1004, (84 pages).
Reply to the communication about intention to grant a European patent under Rule 71(3) EPC dated Apr. 8, 2024, for European Patent Application No. 19811784.8-1004, (8 pages).
Decision to grant a European patent pursuant to Article 97(1) EPC

(56) References Cited

OTHER PUBLICATIONS dated Apr. 18, 2024, for European Patent Application No. 19811784.8-1004, (2 pages).

* cited by examiner

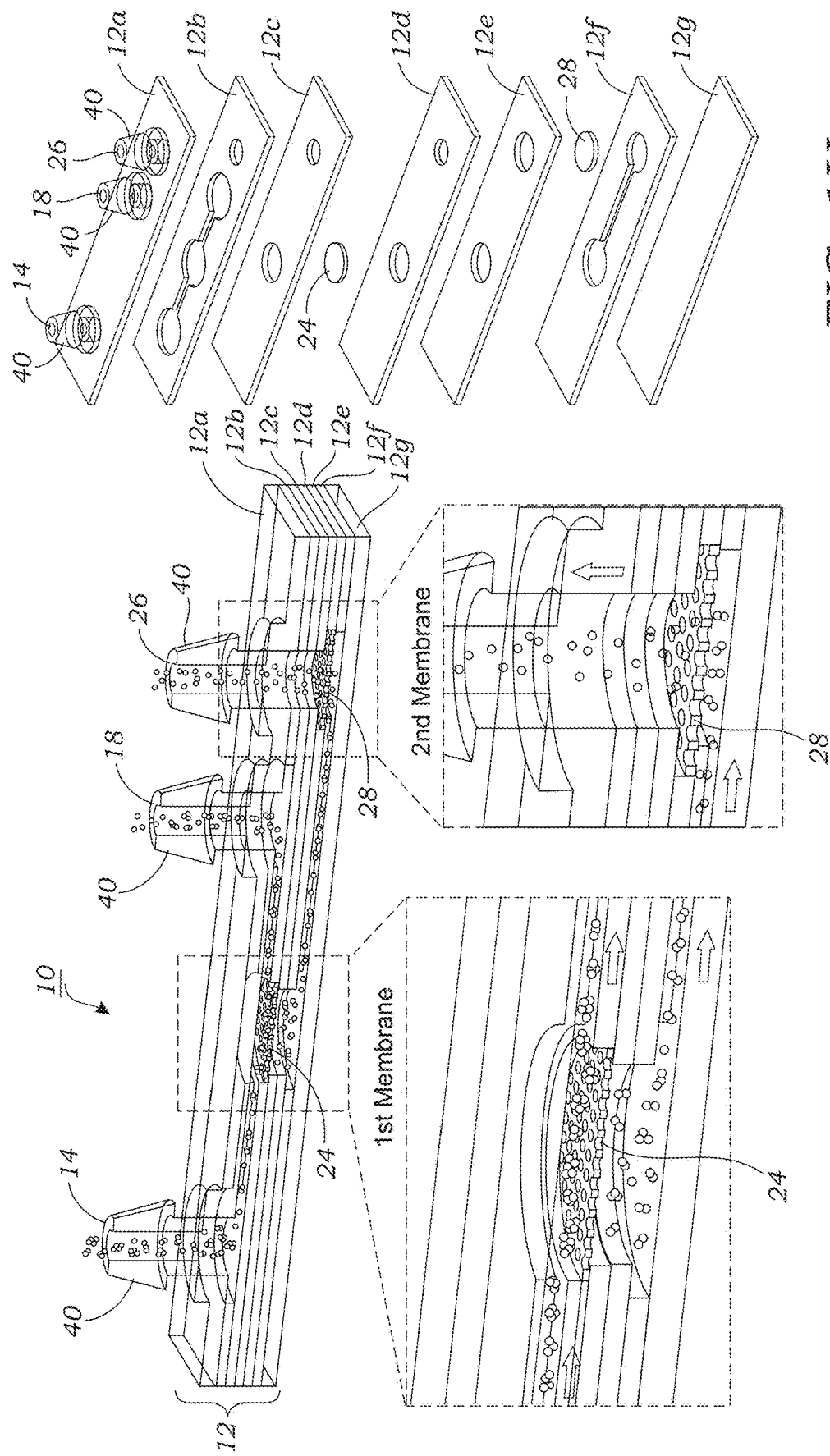

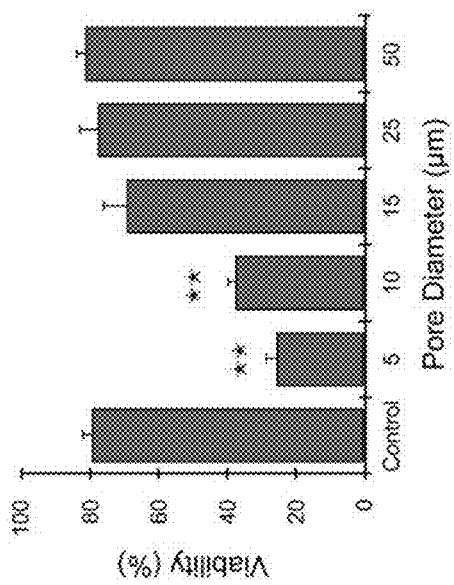
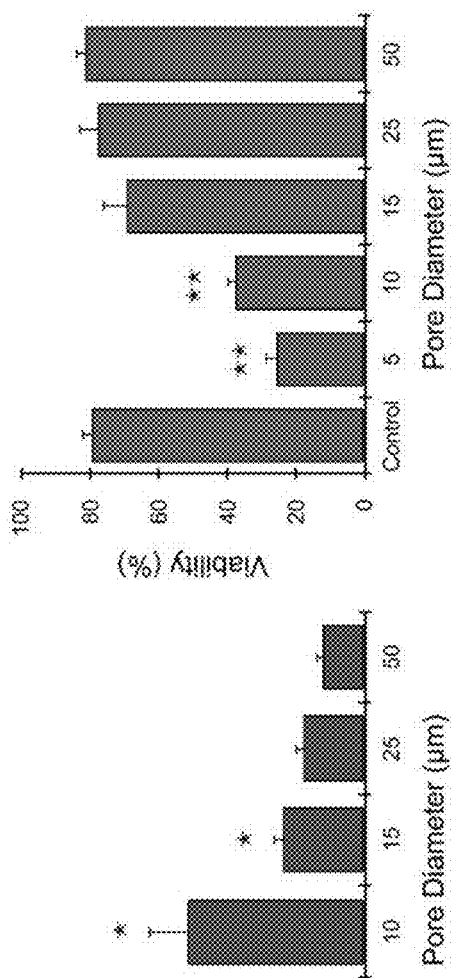
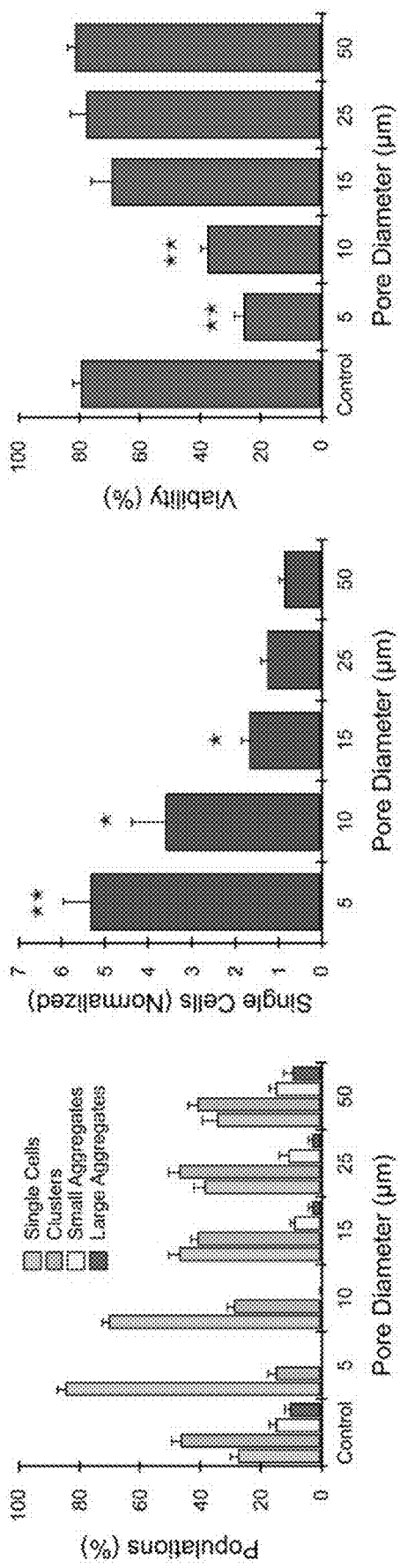
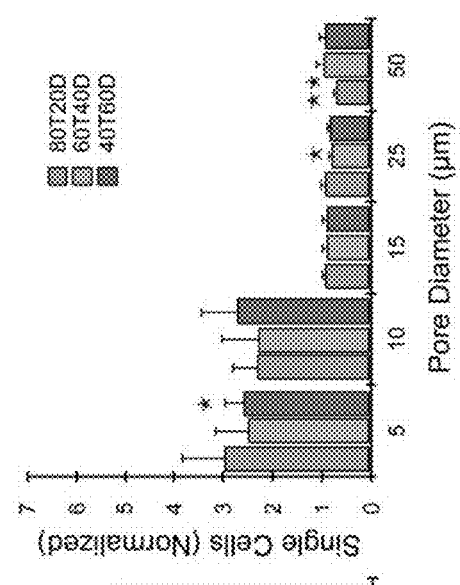
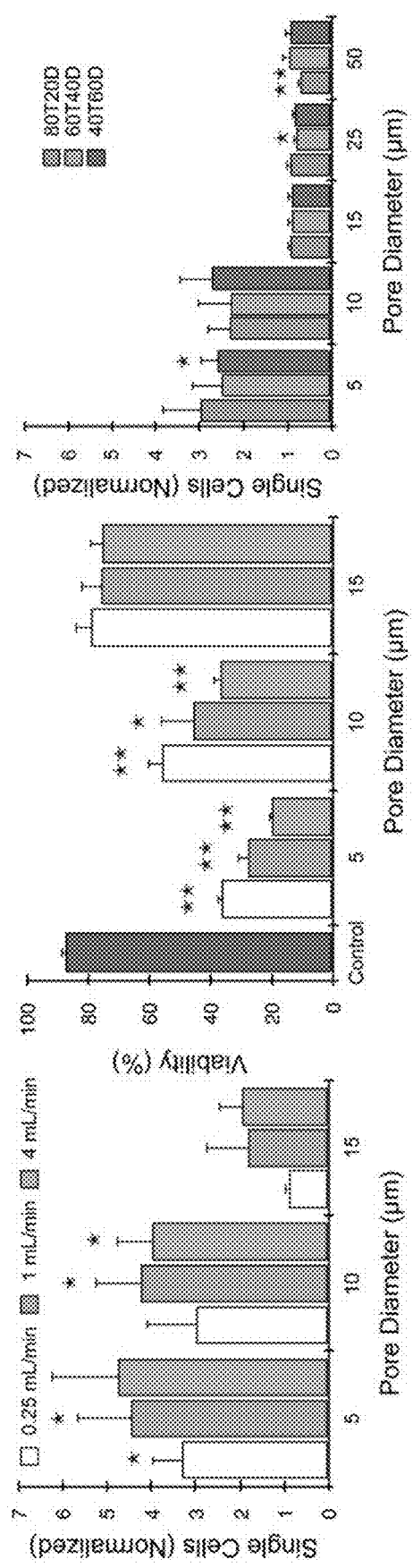
FIG. 3A  FIG. 3B  FIG. 3C
FIG. 3D  FIG. 3E  FIG. 3F

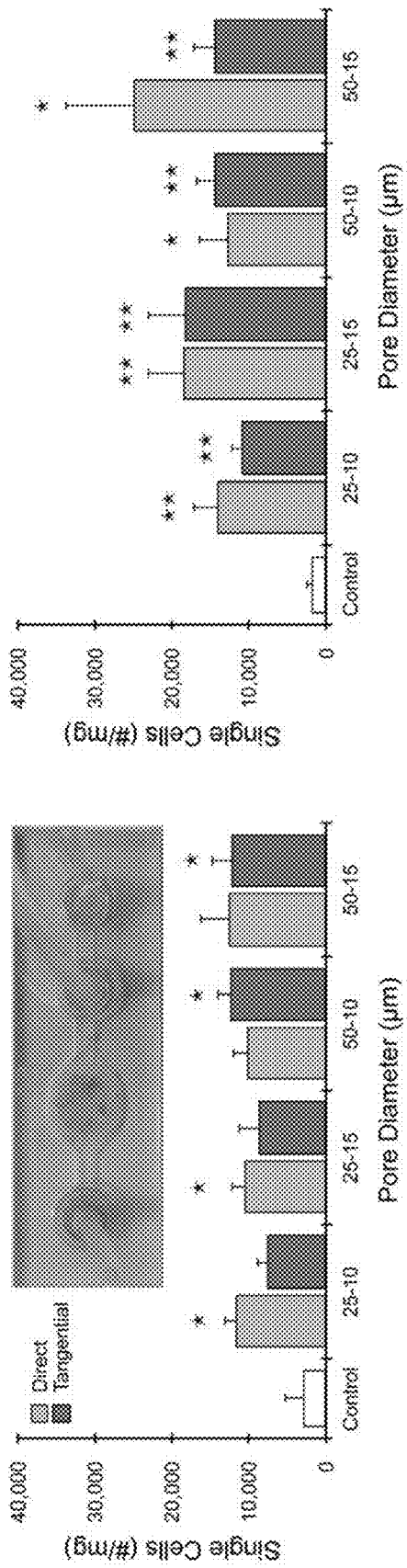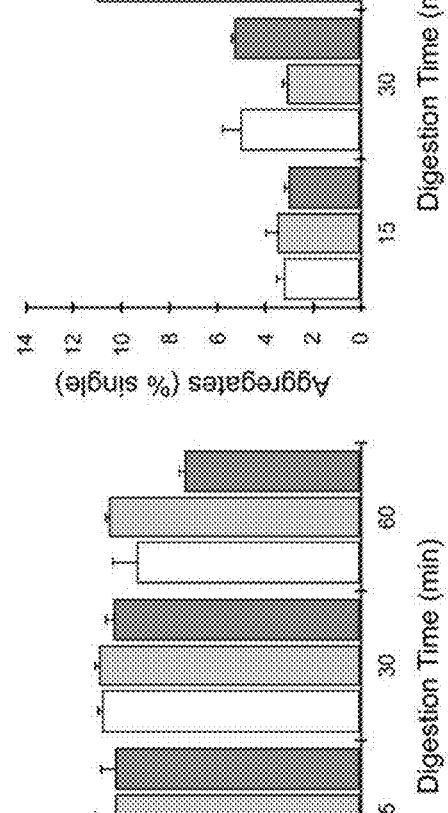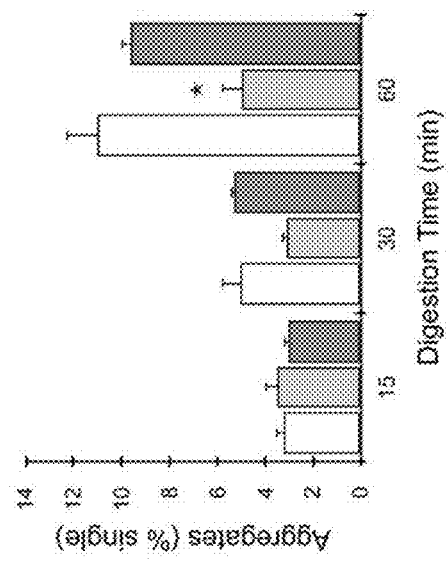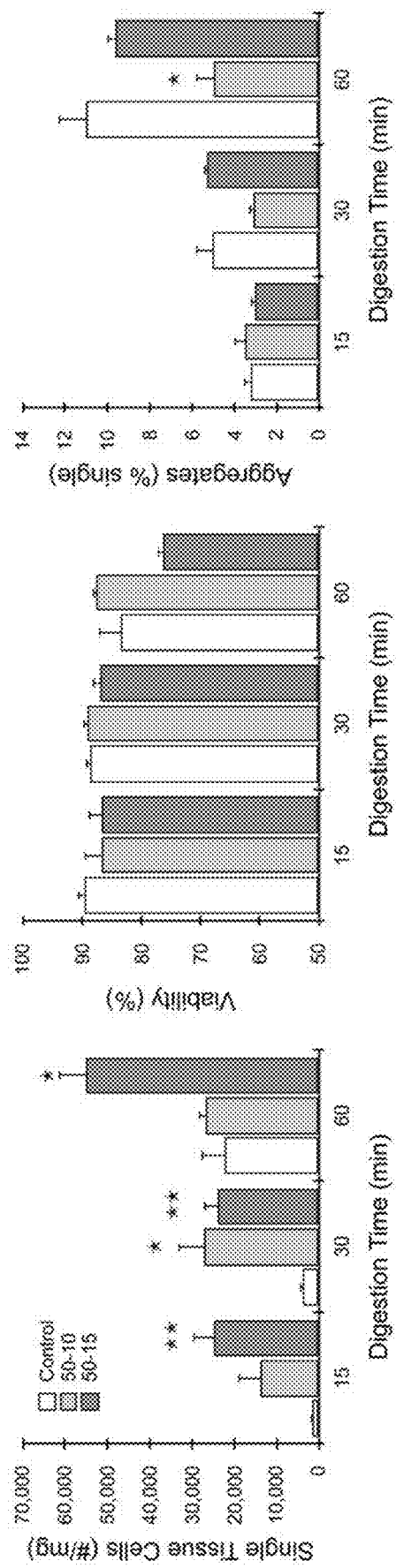
FIG. 5A FIG. 5B FIG. 5C FIG. 5D FIG. 5E

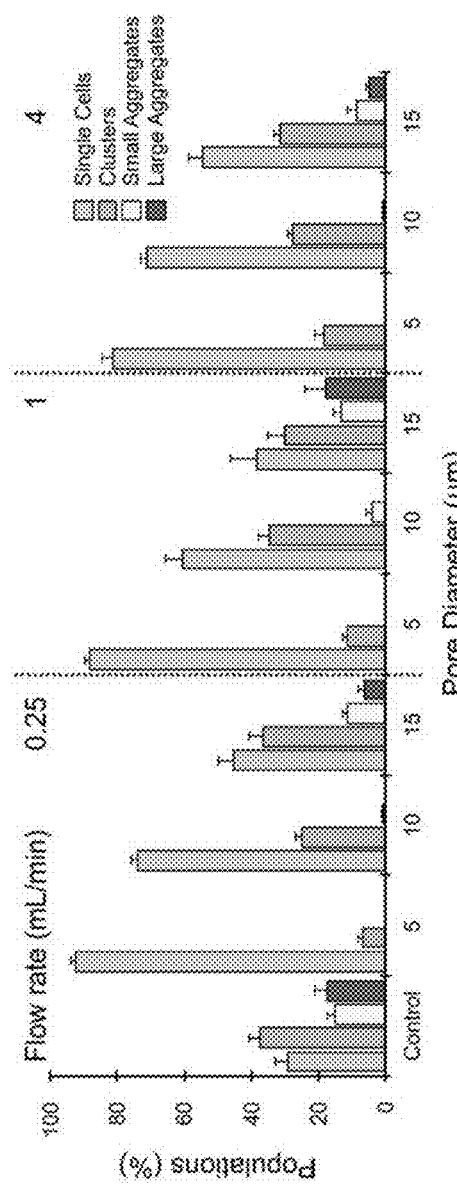
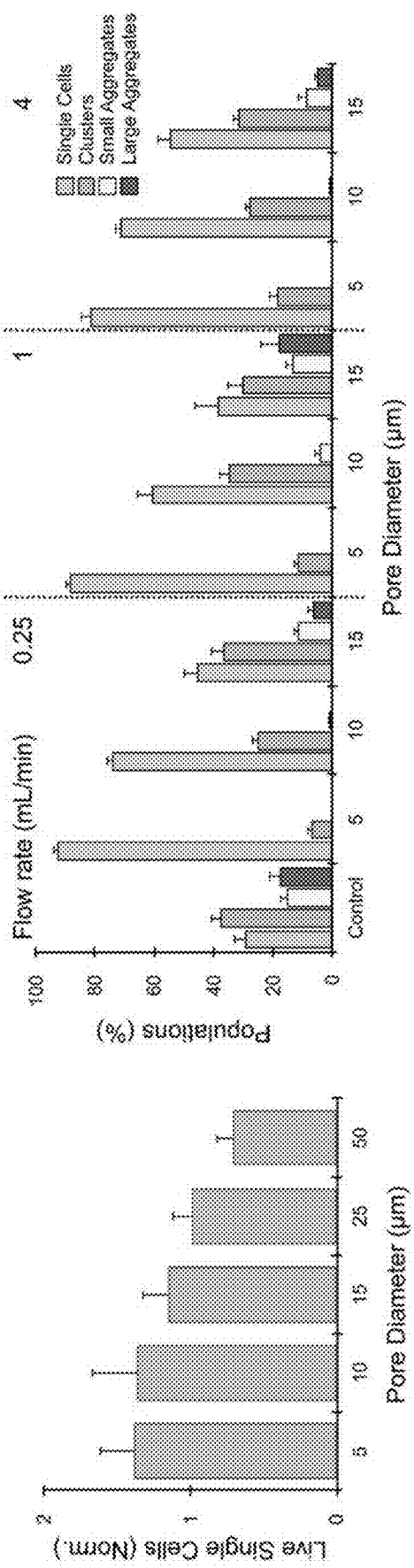
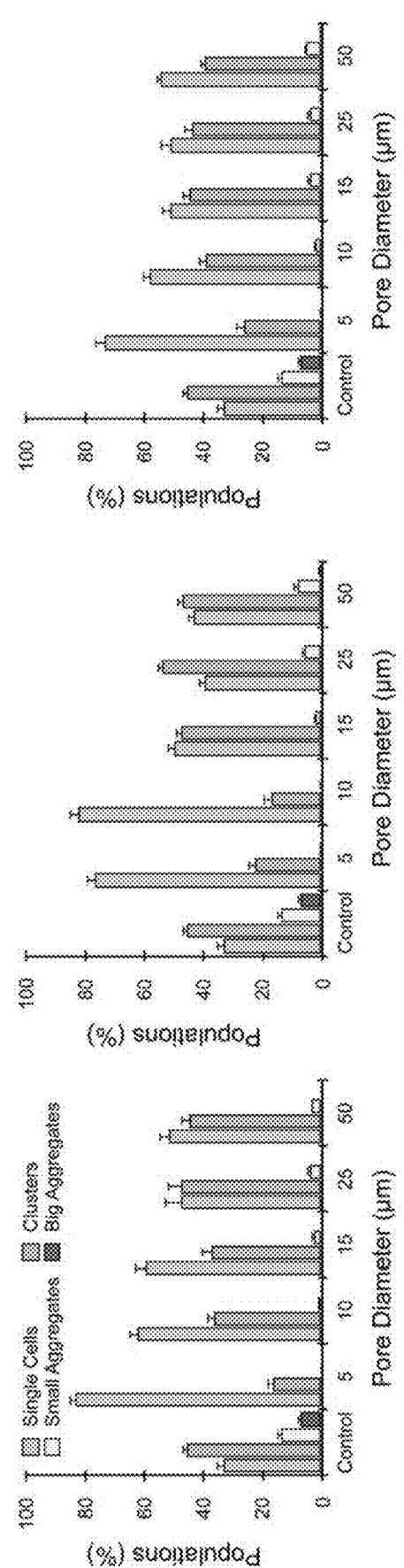

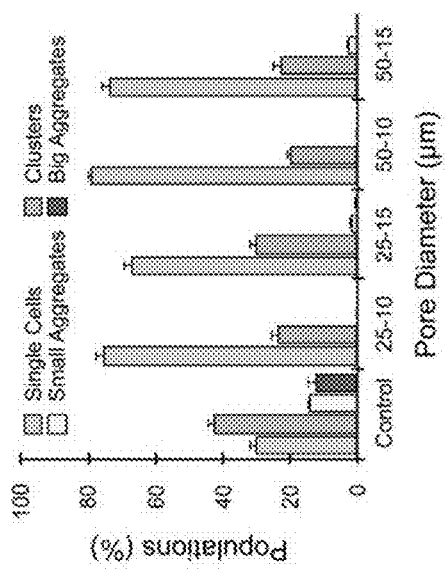
*FIG. 8A*
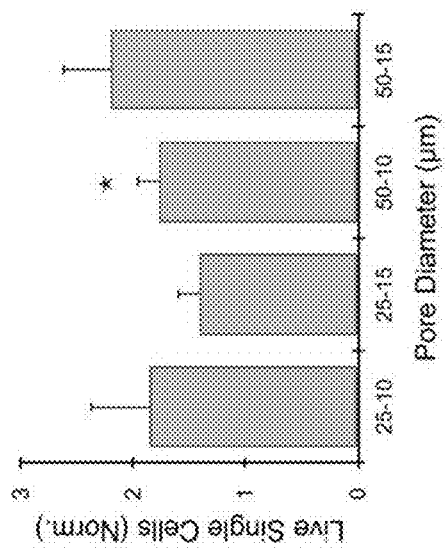
*FIG. 8B*
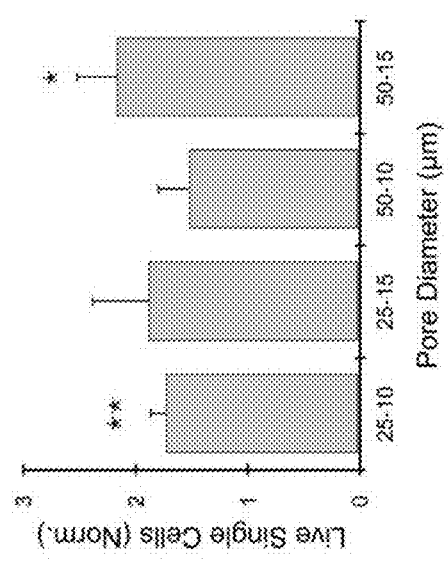
*FIG. 8C*
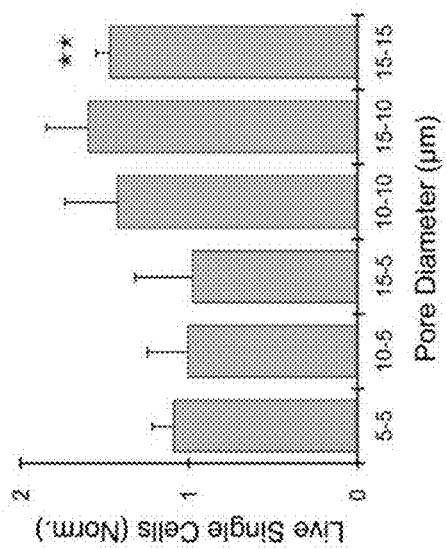
*FIG. 8D*
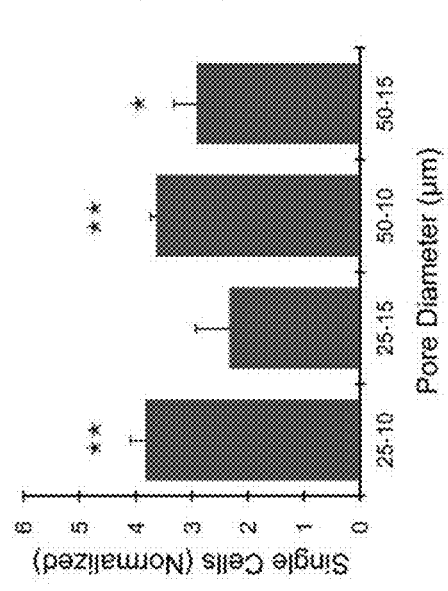
*FIG. 8E*
*FIG. 8F*

MICROFLUIDIC FILTER DEVICE AND METHOD FOR DISSOCIATION OF TISSUE AND CELL AGGREGATES AND ENRICHMENT OF SINGLE CELLS

RELATED APPLICATION

This Application is a U.S. National Stage filing under 35 U.S.C. § 371 of International Application No. PCT/US2019/034470, filed May 29, 2019, which claims priority to U.S. Provisional Pat. Application No. 62/678,171 filed on May 30, 2018, which are hereby incorporated by reference. Priority is claimed pursuant to 35 U.S.C. §§ 119, 371 and any other applicable statute.

STATEMENT REGARDING FEDERALLY SPONSORED RESEARCH AND DEVELOPMENT

This invention was made with Government support under Grant No. IIP1362165, awarded by the National Science Foundation. The Government has certain rights in this invention.

TECHNICAL FIELD

The technical field generally relates to microfluidic devices and methods for obtaining single cells from tissue fragments and cell aggregates. More particularly, the invention pertains to an inexpensive microfluidic device that simultaneously filters large tissue fragments and dissociates smaller aggregates into single cells, thereby improving single cell yield and purity.

BACKGROUND

Complex tissues are increasingly being analyzed at the single cell level in an effort to catalogue diversity and identify rare driver cells. This analysis may provide a comprehensive cell census that could be used to better understand tissue or organ biology, as promoted by, for example, the Human Cell Atlas initiative, as well as improve the diagnosis and treatment of major diseases including solid tumors. Cell-based diagnostic technologies such as flow cytometry, mass cytometry, and single cell RNA sequencing are ideally positioned to meet the above goals but a major limitation is the need to first break tissue down into a suspension of single cells. Traditionally, tissue has been dissociated by mincing into small pieces with a scalpel, digesting with proteolytic enzymes, mechanically dissociating with a pipette and/or vortexing followed by filtering with a cell strainer to remove the remaining aggregates. Microfluidic technologies have recently been developed to automate and improve tissue dissociation, including on-chip digestion and disaggregation using sharp surface edges, post arrays, and branching channel networks that generate hydrodynamic fluid jets.

While these devices have improved processing speed and single cell yield, it has been found that a significant number of small aggregates invariably remain after processing. Large tissue fragments and cell aggregates are commonly removed from digested tissue samples using cell strainers that contain Nylon® mesh filters with pore sizes in the range of 35-80 µm. These pores are large enough to allow small aggregates and clusters to pass through along with the single cells. While cell strainers with smaller pore sizes are available, they are typically avoided due to concern over losing single cells. Eliminating these aggregates by enhancing dissociation power or providing an on-chip separation mechanism would improve the quality of single cell suspensions and enable immediate downstream analysis.

SUMMARY

In one embodiment, a microfluidic tissue dissociation and filtration device is provided that includes an inlet coupled to a first microfluidic channel at an upstream location, the first microfluidic channel coupled to a first outlet at a downstream location. A first filter membrane is interposed between the first microfluidic channel and a second microfluidic channel, wherein the second microfluidic channel is in fluidic communication with the first microfluidic channel via the first filter membrane. A second outlet is coupled to a downstream location of the second microfluidic channel. The first outlet accommodates the passage of fluid and contents that do not pass through the first filter membrane while the second outlet accommodates the passage of fluid and cells or smaller cell aggregates that pass through the first filter membrane. In some embodiments, the second microfluidic channel includes a second filter membrane interposed between the second outlet and the second microfluidic channel. The second filter membrane preferably includes pore sizes that are smaller than the pore sizes contained in the first filter membrane so that additional filtration can take place.

In one embodiment, the microfluidic tissue dissociation and filtration device may be made from a plurality of separate substrates or layers that are bonded or otherwise adhered to one another to make a laminate structure. These substrates or layers may be polymer-based and then adhered to one another to make the final, monolithic structure formed from multiple layers. The first microfluidic channel may be located in one (or more) of these layers while the second microfluidic channel may be located in one (or more) different layers. Vias, holes, or apertures formed in other layers may be used to fluidically connect the first microfluidic channel and the second microfluidic channel (or additional channels) as well as hold the respective filter membranes.

Placing the filter membrane(s) within the microfluidic device minimizes hold-up volume and improves wash efficiency. Moreover, a microfluidic tissue dissociation and filtration device can be operated at high flow rate (>10 mL/min) and can readily be integrated with the other hydrodynamic tissue digestion and aggregate dissociation technologies.

In one embodiment, the filter membrane(s) is/are made from polymeric threads that form a woven mesh. For example, the filter membrane(s) may be made from polyamide threads that create well defined, micron-sized pores. While the particular pore size that is utilized may depend on the nature of the cell that is to be filtered. Typically, the pores range in size from about 5 µm to about 1,000 µm and more preferably within the range from about 10 µm to about 1,000 µm or from about 5 µm to about 100 µm. In one embodiment, the first filter membrane has pores having diameters of $d_1$ and the second filter membrane has pores having diameters of $d_2$, wherein $d_1 > d_2$. For example, in one embodiment, the first filter membrane has pores with a diameter within the range of 15 µm and 1,000 µm while the second filter membrane has smaller diameter pores within a range of 5 µm and 100 µm. This later embodiment involves a multi-stage microfluidic tissue dissociation and filtration device. For the size-based separation of circulating tumor cells (CTCs) from smaller blood cells, pore sizes, in one embodiment, may range from 5-10 μm. Flow rates may range over a wide range of flows depending on the application. For example, for CTC filtration using the microfluidic tissue dissociation and filtration device, flow rates may range from mL/hr for whole blood to 10 mL/min for diluted blood. For other tissue such as fat tissue larger pores may be used, for example, pores within the range of 500 μm-1,000 μm.

In one embodiment, a microfluidic tissue dissociation and filtration device integrates polyamide (e.g., Nylon®) mesh membranes with pore sizes ranging from 5 to 50 μm into laser micro-machined, laminated plastic, or polymer-based microfluidic devices. The microfluidic tissue dissociation and filtration device may operate under a traditional direct filtration mode, with sample passing through the filter membrane, or a tangential filtration mode that utilizes a cross-flow to prevent membrane clogging, or a combination of both. Using cancer cell lines, it was demonstrated that that Nylon® membranes with 10 μm pores or smaller remove all aggregates containing four or more cells, even when operated at high flow rates (mL/min). However, some clusters of 2 to 3 cells still pass through pores that are as small as 5 μm. Interestingly, it was observed that single cell numbers increase significantly after passing pore sizes that are smaller than the cells, by as much as five-fold, but this is also correlated with cell damage. It was also found that dissociation is only weakly dependent on flow rate through the membrane, but is significantly diminished by the presence of a cross-flow under the tangential filtration mode.

In another embodiment, single cell recovery and purity were enhanced by coupling two filter devices in series, such that aggregates are progressively dissociated into smaller sizes. Results predominantly correlate with the pore size of the second membrane, which is smaller and invariably used in direct filtration mode. Next, the performance was optimized using minced and digested murine kidney tissue samples. It was found that the combination of 50 μm and 15 μm pore size membranes produces the most single cells. Finally, the 50 μm (first filter membrane) and 15 μm (second filter membrane) pore size membranes were integrated into a single microfluidic tissue dissociation and filtration device and the results were validated using murine kidney, liver, and mammary tumor tissue samples. After mincing and digesting with collagenase, the dual-membrane microfluidic tissue dissociation and filtration device increases single cell yield by at least 3-fold, and in some cases by more than 10-fold, while also maintaining cell viability and reducing aggregates. Most strikingly, using the microfluidic tissue dissociation and filtration device, after a brief 15 min digestion period, produces as many single cells as a 60 min digestion. Reducing processing time in this manner would help preserve cell viability, phenotype, and molecular signatures for subsequent molecular analysis. The dual-membrane microfluidic filter device may be integrated with upstream tissue processing technologies, such as hydro-mincing and branching channel array, to maximize dissociation speed and efficiency for various tissue types. The device may be used to create complete tissue analysis platforms by integrating the dual membrane microfluidic filter device with additional upstream tissue processing technologies, as well as downstream operations such as cell sorting and detection.

In one embodiment, a microfluidic tissue dissociation and filtration device includes an inlet coupled to a first microfluidic channel at an upstream location, the first microfluidic channel coupled to a first outlet at a downstream location and a first filter membrane interposed between the first microfluidic channel and a second microfluidic channel, wherein the second microfluidic channel is in fluidic communication with the first microfluidic channel via the first filter membrane. A second outlet is coupled to a downstream location of the second microfluidic channel.

In another embodiment, a microfluidic tissue dissociation and filtration device includes an inlet coupled to a first microfluidic channel at an upstream location, the first microfluidic channel coupled to a first outlet at a downstream location, wherein the first microfluidic channel is disposed in a first layer of the microfluidic tissue dissociation and filtration device. The device includes a second microfluidic channel located within a second layer of the microfluidic device and a first filter membrane interposed between the first microfluidic channel and the second microfluidic channel, wherein the second microfluidic channel is in fluidic communication with the first microfluidic channel by a connecting passageway containing the first filter membrane. A second outlet is coupled to a downstream location of the second microfluidic channel and a second filter membrane is interposed between the second outlet and the second microfluidic channel.

In another embodiment, a microfluidic tissue dissociation and filtration device includes an inlet coupled to a first microfluidic channel at an upstream location, the first microfluidic channel coupled to a first outlet at a downstream location, wherein the first microfluidic channel is disposed in a first layer of the microfluidic tissue dissociation and filtration device. A second microfluidic channel is located within a second layer of the microfluidic device and a first filter membrane interposed between the first microfluidic channel and the second microfluidic channel, wherein the second microfluidic channel is in fluidic communication with the first microfluidic channel by a connecting passageway containing the first filter membrane. The device includes a second outlet coupled to a downstream location of the second microfluidic channel and a second filter membrane interposed between the second outlet and the second microfluidic channel. The device further includes one or more additional microfluidic channels disposed in different layers of the microfluidic tissue dissociation and filtration device wherein each of the one or more additional microfluidic channels has respective outlets coupled thereto and respective filter membranes interposed between adjacent microfluidic channels. In this embodiment, the microfluidic tissue dissociation and filtration device may include 3, 4, 5, 6, 7, 8, 9, 10, etc. total filter membranes.

BRIEF DESCRIPTION OF THE DRAWINGS

FIG. 1G illustrates a partial cross-sectional perspective view of a microfluidic tissue dissection device that uses two filters.

FIG. 1H illustrates an exploded view showing the various substrates/layers used to form the microfluidic tissue dissection device of FIG. 1G.

FIG. 3A illustrates a graph showing that single cells, clusters, and aggregates were quantified from micrographs and plotted as percent of total population before (control) and after passing through filter devices containing one membrane with the indicated pore size. Devices were operated in direct filtration mode using a flow rate of 12.5 m/min. Aggregates and clusters were removed with increasing efficiency as pore size decreased, with single cells starting at less than 30% and reaching a maximum of 85%.

FIG. 3B illustrates a graph of single cell numbers quantified using a cell counter and normalized by the control. Significantly more single cells were recovered following filtration through the 5, 10, and 15 μm pore sizes, indicating dissociation of aggregates into single cells.

FIG. 3C illustrates a graph of viability as a function of pore size. Viability was determined by propidium iodide exclusion assay, and decreased with pore size.

FIG. 3D illustrates a graph of normalized single cell counts as a function of pore diameter (direct flow through membrane) at lower flow rates, which generally resulted in less single cell number.

FIG. 3E illustrates a graph of viability percentage as a function of pore diameter (direct flow through membrane) at lower flow rates, which generally resulted in higher viability, although changes were modest.

FIG. 3F illustrates a graph of normalized single cell counts as a function of pore diameter for tangential filtration experiments using different cross-flow ratios (40 to 80%), which resulted in substantially lower single cell numbers than direct flow experiments at 12.5 mL/min. For all FIGS. 3A-3F, error bars represent standard errors from at least three independent experiments. * indicates $p<0.05$ and ** indicates $p<0.01$ relative to the control.

FIG. 4E shows single cell recovery, and FIG. 4F shows viability were all dictated primarily by the pore size of the second membrane. Error bars represent standard errors from at least three independent experiments. * indicates $p<0.05$ and ** indicates $p<0.01$ relative to the control.

FIGS. 5A-5E illustrates the results of freshly harvested kidney tissue that was minced and digested with collagenase before passing through the two filter devices that were coupled in series. FIGS. 5A and 5B illustrate the evaluation of the 25 or 50 μm membranes combined with the 10 or 15 μm membranes, performed under direct or tangential (60% cross-flow) filtration modes. Single cell count was determined using a cell counter. As seen in FIG. 5A, after 15 min digestion, device treatment increased single cell recovery by 2- to 4-fold for all membrane combinations and filtration modes. Inset image shows tissue captured on a 50 μm pore size membrane. FIG. 5B illustrates how device treatment increased single cell recovery by more than 5-fold for all cases after 30 min digestion. Results were generally based on the second membrane pore size, and did not vary significantly with the first membrane pore size or filtration mode. FIGS. 5C-5E illustrates results of the investigation of the 50-10 and 50-15 combinations using flow cytometry. FIG. 5C shows single tissue cells numbers recovered from the 50-15 and 50-10 membrane combination exceeded controls by 5- to 10-fold at the 15 and 30 min digestion times. After 60 min digestion, the 50-15 μm combination enhanced single tissue cell recovery by 2.5-fold. FIG. 5D shows that viability was 90% for all conditions at the 15 and 30 min digestion times, but decreased after 60 min digestion to 80% for the control and 75% for the 50-15 μm filter combination. FIG. 5E illustrates aggregate and cluster numbers were quantified using scattering information and are presented relative to single cells. Aggregates increased with digestion time for controls, remained the same using the 50-15 membrane combination, but decreased for the 50-10 membrane combination. Error bars represent standard errors from at least three independent experiments. * indicates $p<0.05$ and ** indicates $p<0.01$ relative to the control at the same digestion time.

As seen in FIG. 6A, device treatment increased single liver tissue cells by 5-fold and 2-fold after 15 and 30 min digestion, respectively. The device did not increase single liver tissue cells further after 60 min, as enzymatic digestion had fully liberated cells. With reference to FIG. 6B, viability remained greater than 90% for controls and device conditions. As seen in FIG. 6C, aggregates were present at 1% for controls at all digestion times, and were generally reduced by device treatment. In FIG. 6D, device treatment increased single epithelial cells by 3-fold at all digestion times. As seen in FIG. 6E, cell viability was significantly lower for tumors at 40-50%, but did not vary significantly with digestion time or device treatment. Aggregates constituted about 15-20% of cell suspensions for all conditions (FIG. 6F). Error bars represent standard errors from at least three independent experiments. * indicates $p<0.05$ and ** indicates $p<0.01$ relative to the control at the same digestion time.

FIGS. 7A-7E illustrate single filter device experiments using MCF-7 cells. FIG. 7A shows live single cell numbers for experiments performed under direct filtration mode and 12.5 mL/min flow rate. Values were 40% higher than the control for each of the 5, 10, and 15 μm pore sizes. FIG. 7B illustrates cell populations obtained for direct filtration experiments at 0.25, 1, and 4 mL/min flow rates. FIGS. 6C-6E illustrate cell populations obtained for tangential filtration experiments using 12.5 mL/min total flow rate and cross-flow ratios of 80% (FIG. 7C), 60% (FIG. 7D), and 40% (FIG. 7E). Error bars represent standard errors from at least three independent experiments. * indicates $p<0.05$ and ** indicates $p<0.01$ relative to the control.

FIGS. 8A-8F illustrate double filter device experiments using MCF-7 cells. FIG. 8A illustrates live single cell number for double filter device experiments performed under direct filtration mode and 12.5 m/min flow rate. Values were lowest for membrane all combinations that included the 5 μm pore size. FIG. 8B Live single cell numbers for double filter device experiments performed under tangential filtration mode, 12.5 m/min total flow rate, and 60% cross-flow ratio. Values were close to 2-fold greater than control in all cases.

FIGS. 8C-8F illustrate the results of double filter device experiments performed under tangential filtration mode, 12.5 mL/min total flow rate, and 80% cross-flow ratio. Results for cell populations (FIG. 8C), single cell recovery (FIG. 8D), viability (FIG. 8E), and live single cell recovery (FIG. 8F) were similar to 60% cross-flow ratio experiments. Error bars represent standard errors from at least three independent experiments. * indicates $p<0.05$ and ** indicates $p<0.01$ relative to the control.

FIGS. 9A, 9B experiments performed using two single membrane filter devices connected in series. Recoveries are shown for FIG. 9A red blood cells and FIG. 9B leukocytes, which both increased with both digestion time and device processing in a manner consistent with single tissue cell recovery results in FIG. 5C. FIGS. 9C, 9D illustrate experiments performed using the integrated dual membrane filter device with kidney tissue that was digested for 60 min. Single tissue cell number increased by ~60% after device processing relative to the control (FIG. 9C). Viability remained at >85%, similar to control (FIG. 9D). Error bars represent standard errors from at least three independent experiments. * indicates $p<0.05$ and ** indicates $p<0.01$ relative to the control at the same digestion time.

DETAILED DESCRIPTION OF ILLUSTRATED EMBODIMENTS

Figure 1A:
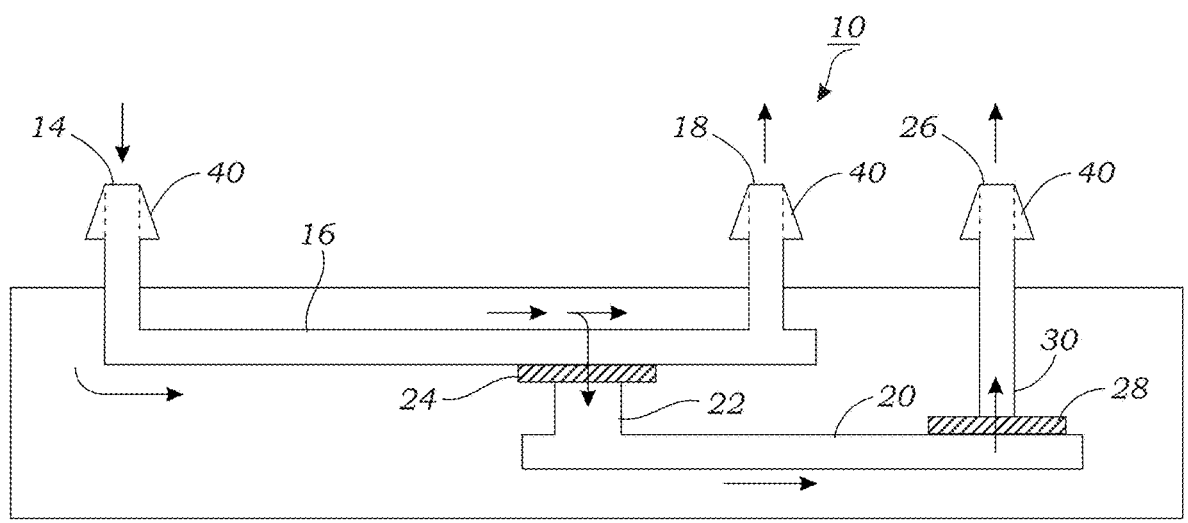
FIG. 1A illustrates a cross-sectional view of a microfluidic tissue dissociation and filtration device according to one embodiment that includes two (2) filters in series.
Figure 1B:
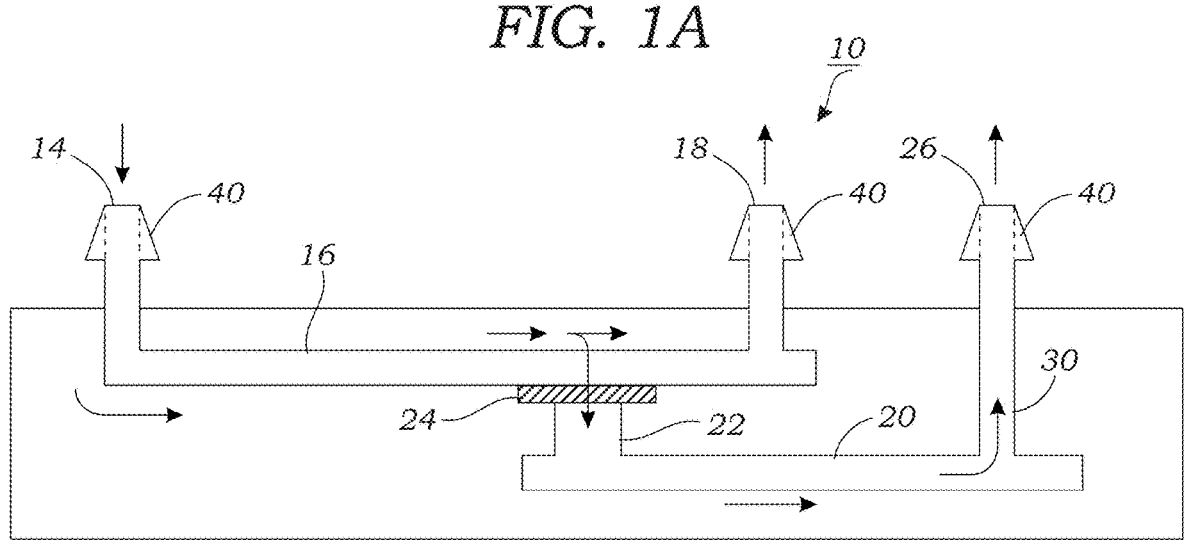
FIG. 1B illustrates a cross-sectional view of a microfluidic tissue dissociation and filtration device according to one embodiment that includes one (1) filter.

FIG. 1A illustrates a cross-sectional view of the microfluidic tissue dissociation and filtration device 10 according to one embodiment. The microfluidic tissue dissociation and filtration device 10 is formed in one or more substrates or layer 12 as best illustrated in FIGS. 1D, 1E, 1F, 1G, and 1H. The substrates or layers 12 may be formed from a polymer or plastic material that contains various features formed therein that are laminated or otherwise bonded together to form the final microfluidic tissue dissociation and filtration device 10 according to one embodiment. The various features formed in the substrates or layers 12 include the channels and fluid passageways (described below in more detail) through which fluid flows during operation of the microfluidic tissue dissociation and filtration device 10.

The microfluidic tissue dissociation and filtration device 10 includes an inlet 14 through which fluid flows into the microfluidic tissue dissociation and filtration device 10. The inlet 14 may include a barbed end 40 or the like as illustrated that can be connected to tubing or other conduit that is used to deliver the fluid containing tissue to the microfluidic tissue dissociation and filtration device 10. The inlet 14 is fluidically coupled to a first microfluidic channel 16 at an upstream location (arrows indicate the direction of fluid flow). The first microfluidic channel 16 is also coupled to a first outlet 18 that is located at a downstream location. The first outlet 18 may include a barbed end 40 or the like as illustrated that can be connected to tubing or other conduit that is used to remove fluid containing cells and cell aggregates from the microfluidic tissue dissociation and filtration device 10. The first microfluidic channel 16 is at least partially defined in one or more of the substrates or layers 12. For example, the surfaces (top, bottom, sides) of the first microfluidic channel 16 may be defined in the one or more of the substrates or layers 12. The typical cross-sectional dimension of the first microfluidic channel 16 may include a height within the range of about 200 μm to about 1 mm and a width within the range of about 1 mm to about 1 cm. The length of the first microfluidic channel 16 (from end to end) may vary from a few centimeters and tens or even hundreds of centimeters (e.g., from about 5 cm to about 100 cm in one example). It should be appreciated that these dimensions are illustrative.

With reference to FIG. TA, the microfluidic tissue dissociation and filtration device 10 includes a second microfluidic channel 20. The second microfluidic channel 20 is, in one embodiment, disposed in a different substrate or layer 12 of the microfluidic tissue dissociation and filtration device 10 as seen in FIGS. 1D, 1E, 1F, 1G, and 1H. In this regard, the second microfluidic channel 20 is located in a different plane than the first microfluidic channel 16. For example, the second microfluidic channel 20 may be located in a lower plane than the first microfluidic channel 16. Like the first microfluidic channel 16, the second microfluidic channel 20 may be defined in the one or more of the substrates or layers 12. The typical cross-sectional dimension of the second microfluidic channel 20 may include a height within the range of about 200 μm to about 1 mm and a width within the range of about 1 mm to about 1 cm. The length of the second microfluidic channel 20 (from end to end) may vary from a few centimeters and tens or even hundreds of centimeters (e.g., from about 5 cm to about 100 cm in one example). It should be appreciated that these dimensions are illustrative.

The second microfluidic channel 20 is fluidically connected to the first microfluidic channel 16 by a fluid passageway 22. The fluid passageway 22 that connects the second microfluidic channel 20 to the first microfluidic channel 16 may include a via, hole, or aperture that extends between the first microfluidic channel 16 to the second microfluidic channel 20. The fluid passageway 22 may be formed or defined in one or more layers 12 that are located between the layers 12 that form the first microfluidic channel 16 and the second microfluidic channel 20. A first filter membrane 24 is disposed in or across the fluid passageway 22 and is interposed between the first microfluidic channel 16 and the second microfluidic channel 20. For example, the first filter membrane 24 may be formed as a single layer of woven mesh polymer thread that is sandwiched between two adjacent layers 12 and extends across the fluid passageway 22. In one embodiment, the thread used for the first filter membrane 24 is polyamide thread (e.g., Nylon®). The pore diameters that make up the first filter membrane 24 may, in one embodiment, may be within the range of about 1 μm to about 100 μm. Pore diameters in this context refers to the nominal or average pore diameter of the particular filter membrane. In another embodiment, the first filter membrane 24 may have pore diameters within the range of about 5 μm to about 50 μm.

Referring to FIG. 1A, the second microfluidic channel 20 is spaced apart from the first microfluidic channel 16 and fluid passes into the second microfluidic channel 20 by entering the fluid passageway 22 and then passing through the first filter membrane 24 (arrows indicate flow direction). In this regard, the second microfluidic channel 20 is in fluidic communication with the first microfluidic channel 16. As seen in FIG. 1A, a second outlet 26 is coupled to a downstream location of the second microfluidic channel 20. The second outlet 26 may include a barbed end 40 or the like as illustrated that can be connected to tubing or other conduit that is used to remove single cells and fluid from the microfluidic tissue dissociation and filtration device 10. A second filter membrane 28 is disposed in or across a fluid passageway 30 that couples the second microfluidic channel 20 to the second outlet 26. The fluid passageway 30 may include a via, hole, or aperture that extends between the second microfluidic channel 20 and the second outlet 26. The fluid passageway 30 may be formed or defined in one or more layers 12 that are located between the layers 12 that form the second microfluidic channel 20 and the top layer 12 that has the second outlet 26. The second filter membrane 28 is disposed in or across the fluid passageway 30 and is interposed between the second microfluidic channel 20 and the second outlet 26. Like the first filter membrane 24, the second filter membrane 28 may be formed as a single layer of woven mesh polymer thread that is sandwiched between two adjacent layers 12 and extends across the fluid passageway 30.

The second filter membrane 28 may be made from similar materials and have similar, albeit smaller pore sizes than the first filter membrane 24. As explained herein, the first filter membrane 24 and the second filter membrane 28 may be formed using single layer, woven meshes of polymer fibers although they may also be formed using microfabricated membranes or track-etched membranes. Track-etched membranes are formed by exposing a membrane material such as polycarbonate or polyester to charged particles. The charged particles pass through the membrane material creating points of weakness. An etchant is then used to eat away the polymer material along the tracks formed by the charged particles. The etchant widens the tracks into pores of defined sizes. Microfabricated membranes may be formed using photolithographic patterning of polymer materials (either positive or negative patterning). Regardless of how they are made the respective filter membranes 24, 28 have pores defined therein. The size of these respective pores is well defined using commonly known manufacturing techniques for filter membranes. Typically, the pores range in size from about 1 μm to about 100 μm and more preferably within the range from about 5 μm to about 50 μm. In one embodiment, the first filter membrane 24 has pores having diameters of $d_1$ and the second filter membrane 28 has pores having diameters of $d_2$, wherein $d_1 > d_2$. This permits progressively smaller filtration of cell aggregates and cells.

As seen in FIG. 1A, the microfluidic tissue dissociation and filtration device 10 contains one (1) inlet 14 and two (2) outlets 18, 26. The first outlet 18 collects tangential flow effluent while the second outlet 26 collects the direct flow effluents that passes through the first filter membrane 24 and the second filter membrane 28. As explained herein, the microfluidic tissue dissociation and filtration device 10 is fabricated, in one preferred embodiment, using a commercial laminate process in which the substrates or layers 12 are thin acrylic sheets that are laser-etched and bonded using adhesive and pressure lamination. In some embodiments, as illustrated in FIGS. 1D, 1E, 1F, 1G, 1H a total of seven (7) plastic layers 12 are used, along with Nylon® mesh filter membranes 24, 28 with well-defined pore sizes in the range of 1-100 μm that are disposed between layers 12 within respective fluid passageways 22, 30. For example, as explained in experiments herein, the mesh filter membranes 24, 28 was tested with pore sizes of 5, 10, 15, 25, and 50 μm. The first microfluidic channel 16 connects the device inlet 14 to the first filter membrane 24 and collects the cross-flow across the first filter membrane 24 via the tangential flow outlet 18. The second microfluidic channel 20 collects the flow through the first filter membrane 24 and directs flow through the second filter membrane 28 and out the second outlet 26. Note that in some embodiments, the first outlet 18 may be plugged or omitted entirely in which case first and second filter membranes 24, 28 operate in direct flow mode with no tangential flow.

FIGS. 1B, 1D, 1E, and 1F illustrate another embodiment of the microfluidic tissue dissociation and filtration device 10. As in the prior embodiment, the microfluidic tissue dissociation and filtration device 10 contains one (1) inlet 14 and two (2) outlets 18, 26. The first outlet 18 collects tangential flow effluent while the second outlet 26 collects the direct flow effluents that passes through the filter membrane 24. In this embodiment, only a single filter membrane 24 is employed. The microfluidic tissue dissociation and filtration device 10 is fabricated using a commercial laminate process in which thin acrylic sheets are laser-etched and bonded using adhesive and pressure lamination. The membrane may include a mesh (e.g., Nylon®) filter membrane 18 with well-defined pore diameter sizes in the range of 5, 10, 15, 25, and 50 μm that is interposed between the first microfluidic channel 14 and the second microfluidic channel 20. In some embodiments, only a single filter membrane 24 is needed, although performance may be improved using two filter membranes 24, 28. In addition, in some embodiments, the first outlet 18 may be plugged or omitted entirely in which case first membrane operates in direct flow mode with no tangential flow.

Figure 1C:
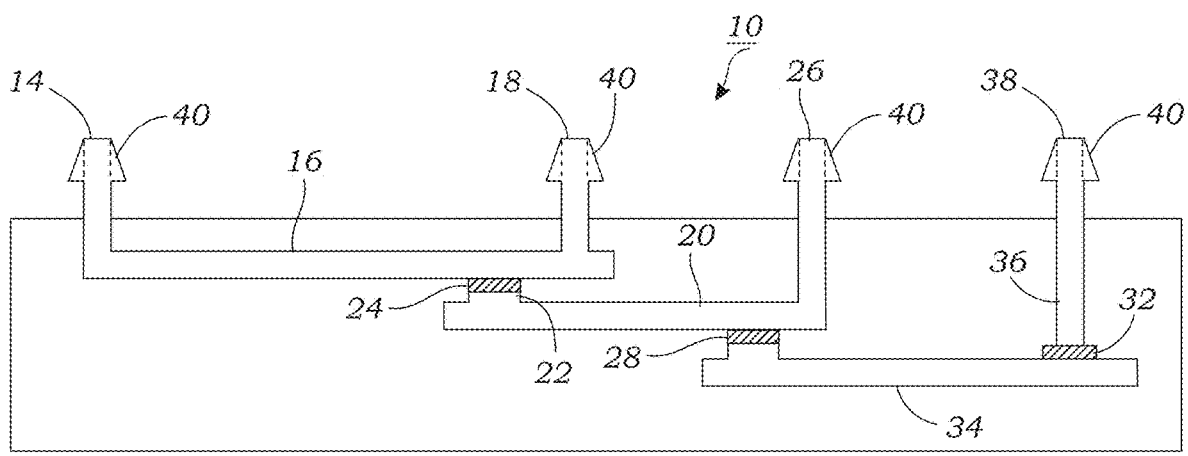
FIG. 1C illustrates a cross-sectional view of a microfluidic tissue dissociation and filtration device according to one embodiment that includes three (3) filters in series.
Figure 1D:
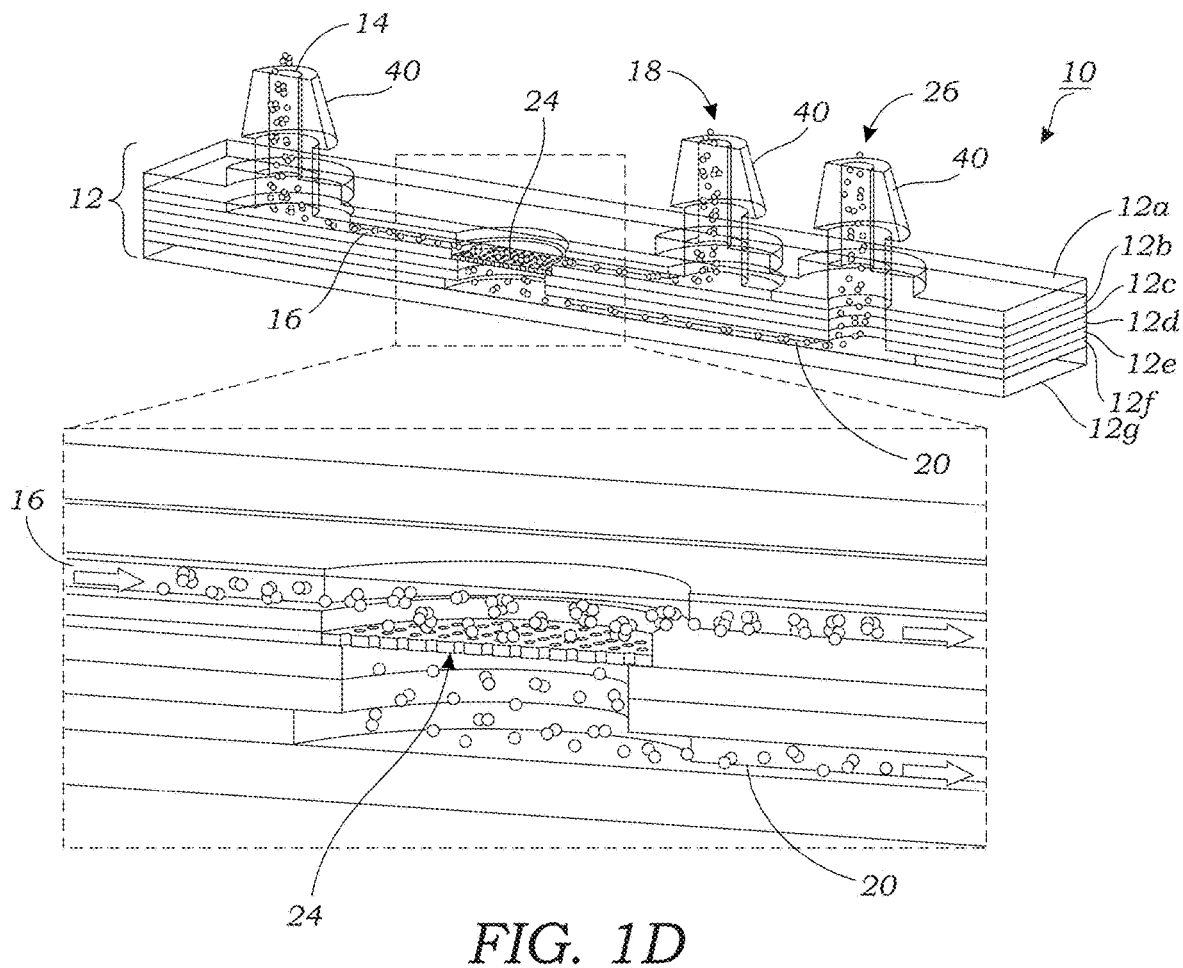
FIG. 1D illustrates a partial cross-sectional perspective view of a microfluidic tissue dissection device that uses a single filter.
Figure 1E:
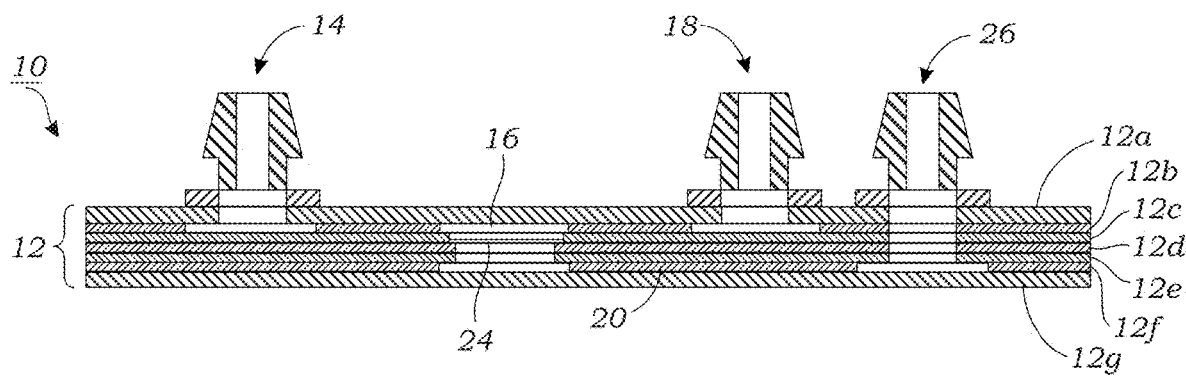
FIG. 1E illustrates a side cross-sectional view of the microfluidic tissue dissection device of FIG. 1E.
Figure 1F:
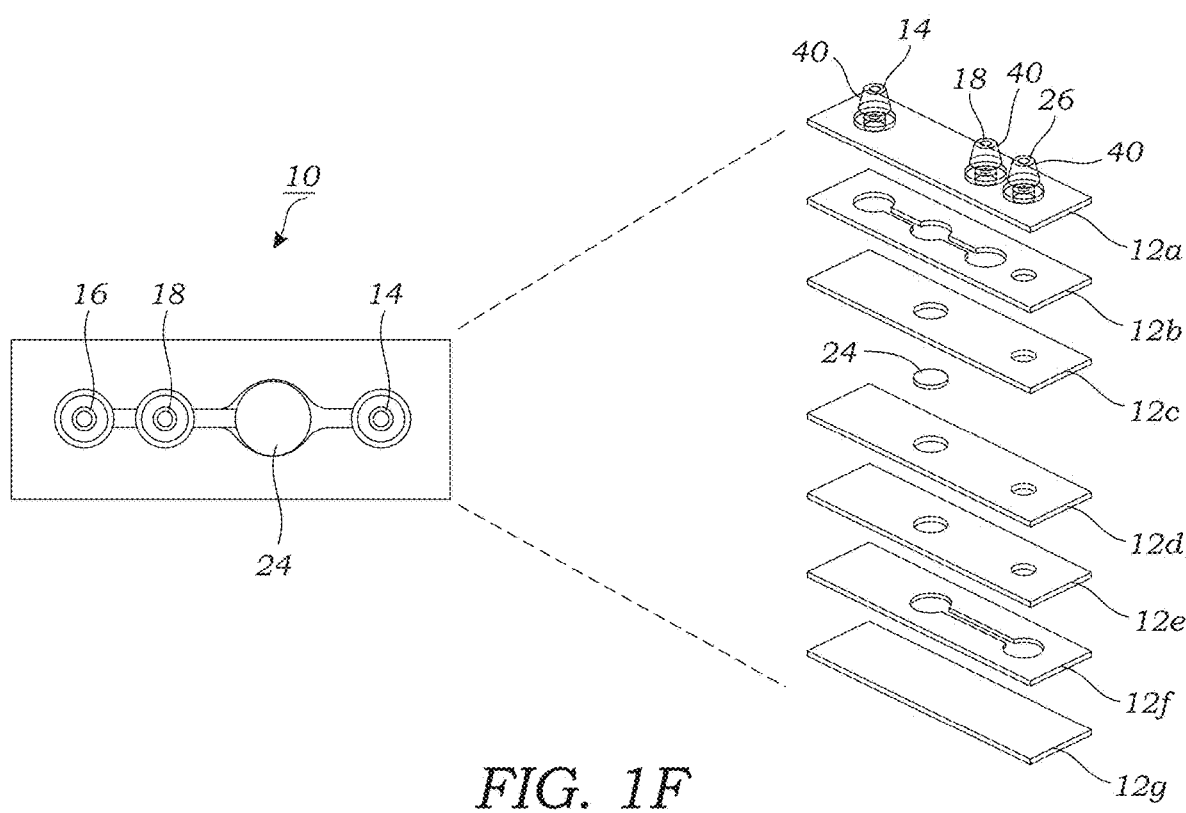
FIG. 1F illustrates a top view of a microfluidic tissue dissection device that uses a single filter along with an exploded view showing the various substrates/layers used to form the microfluidic tissue dissection device.

FIG. 1C illustrates yet another embodiment of a microfluidic tissue dissociation and filtration device 10. This embodiment illustrates a device 10 that utilizes a first filter membrane 24, a second filter membrane 28, and a third filter membrane 32. Similar aspects to the embodiments disclosed in FIGS. 1A and 1B contain similar reference numbers. In this embodiment, the second filter membrane 28 operates on tangential flow with larger aggregates that have passed through the first filter membrane 24 being directed out of the second outlet 26. Smaller aggregates pass through the second filter membrane 28 and enter the third microfluidic channel 34 which leads to the third filter membrane 32. The third filter membrane 32 is located in a fluid passageway 36 that couples the third microfluidic channel 34 to a third outlet 38. The fluid passageway 36 may include a via, hole, or aperture that extends between the third microfluidic channel 34 and the third outlet 38. The fluid passageway 36 may be formed or defined in one or more layers 12 that are located between the layers 12 that form the third microfluidic channel 34 and a top layer 12 that has the third outlet 38. The third filter membrane 32 is disposed in or across the fluid passageway 36 and is interposed between the third microfluidic channel 34 and the third outlet 38. Like the first filter membrane 24, the third filter membrane 32 may be formed as a single layer of woven mesh polymer thread that is sandwiched between two adjacent layers 12 and extends across the fluid passageway 36.

To use any of the microfluidic tissue dissociation and filtration devices 10, a sample solution containing the material to be processed is flowed through the device 10 using, for example, one or more pumps (not shown). Pumps may be provided to push or even pull material through the device 10. Thus, the pumps may be fluidically connected to the inlet 14 or the outlets 18, 26, 38 via tubing or similar types of conduit. In some embodiments, fluid that exits the outlets (e.g., outlets 18, 26) may be recirculated back into the inlet 14 so that the material to be processed makes multiple passes through the microfluidic tissue dissociation and filtration device 10. Numerous biological materials may be processed using the device 10. This includes, by way of example, tissue, tissue fragments, digested tissue, un-digested tissue, and cellular aggregates. The tissue may be healthy tissue or diseased tissue. In some embodiments, the microfluidic tissue dissociation and filtration device 10 may be coupled to other devices at the upstream or downstream ends. For example, tissue dissociation devices such as the hydro-mincing or branched microfluidic device may be coupled upstream of the device 10 where processed tissue leads to the inlet 14. The outlets 18, 26, 38 may be coupled to one or more downstream devices for further processing or analysis of the dissociated cells.

Results and Discussion
Device Design

The microfluidic tissue dissociation and filtration device 10 was designed to remove tissue fragments and cell aggregates produced by standard enzymatic digestion procedures or comparable microfluidic processing. This enhances single cell purity for downstream diagnostic applications, and any aggregates that were retained could be further processed to increase overall cell recovery. A schematic of the device 10 that was used for experiments is shown in FIG. 1A. Sample is introduced via the inlet 14 and comes into contact with a microporous filter membrane 24. Sample that passes through the filter membranes 24, 28 will exit through the effluent outlet. A portion of the sample can also be directed along the surface of the membrane 24 and exit through the cross-flow outlet 18. This arrangement was chosen to maximize device utility by enabling operation in either direct or tangential filtration modes. Under direct filtration, all of the sample would pass through the membrane to maximize sample recovery and processing speed. Under tangential flow, the cross-flow would sweep larger tissue fragments and cell aggregates away from the membrane surface to prevent clogging. However, not all of the sample would be filtered, requiring multiple passes to collect the full sample.

Microfluidic tissue dissociation and filtration devices 10 were fabricated using a commercial laminate approach, with channel features (including channels, vias or holes) were laser micro-machined into hard plastic (polyethylene terephthalate, PET). This provides a more robust device than alternative fabrication methods, such as photolithography and casting of polydimethyl siloxane (PDMS), and thus better supports the high flow rates and pressures that are desired for rapid tissue filtration. A total of seven (7) PET layers 12 were used, including two channel layers 12b, 12f, three via layers 12c, 12d, 12e, and two layers 12a, 12g to seal the device as seen in FIGS. 1D-1H. Two locations were included for mounting thin, microporous filter membranes 24, 28 for the dual filter membrane embodiment of FIGS. 1A, 1G, 1H. The first location is in the center of the device 10, sandwiched between the via layers 12c, 12d, and this filter membrane 24 would be used for either tangential or direct filtration of large tissue fragments and cellular aggregates. It was hypothesized that a second filter membrane 28 with smaller pores could help maximize single cell purity. This second filter membrane 28 (in those embodiments where used such as illustrated in FIGS. 1A, 1G, 1H) was placed immediately upstream of the effluent outlet 26, sandwiched between the bottom channel 12f and via layer 12e and allows for direct filtration of smaller aggregates and clusters. Hose barbs 40 were mounted in the top layer 12a to serve as device inlets 14 and outlets 18, 26. After laser micro-machining, devices 10 were assembled by stacking the various layers 12 and membranes 24, 28 together using adhesive, which were then firmly bonded using pressure lamination. Channel height was ~300 µm, which included contributions from the plastic (250 µm) and adhesive (~50 µm).

Figure 2:
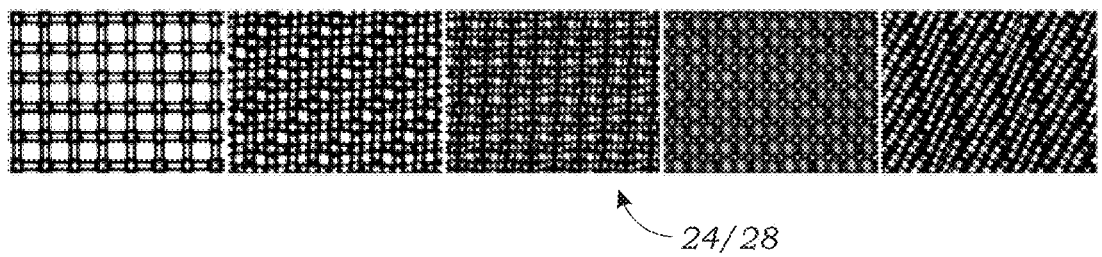
FIG. 2 illustrates micrographs of Nylon® mesh membranes, showing lattice network with high pore density and uniformity. Pore sizes are (left to right) 50, 25, 15, 10, and 5 μm diameter.

For the microporous filter membranes 24, 28, single-layer woven Nylon® meshes were utilized. These are commercially available with pore sizes down to 5 µm from numerous vendors as inexpensive, ready-to-use sheets that can be cut to size. The Nylon® threads create a rigid lattice network with high pore density and uniformity, limit back-pressure and allow for high flow rates through the membrane. Micrographs of the Nylon® mesh membranes used in the experiments described herein are shown in FIG. 2. Moreover, it was hypothesized that the narrow cross-section and rounded shape of the Nylon® threads will be ideal for dissociating aggregates into smaller clusters or even single cells. One would expect a dissociation mechanism to be most prevalent when aggregates are only slightly larger than the pores. This is because aggregates that span many pores are more likely to be captured in a similar manner to traditional filtration. Track-etched membranes were considered, as they are also cheap, easy to use, and have been used extensively in single cell and aggregate filtration studies. However, pores are randomly located and thus tend to overlap at high porosity. Microfabricated membranes offer precise control over pore size, shape, and location and have been used for cell filtration and compartmentalization. However, custom fabrication adds cost and complexity, and the membranes may not be as durable at high porosity. Thus, it was concluded that Nylon® mesh membranes provided the optimal combination of cost and performance characteristics, while also providing potential for aggregate dissociation.

Filtration of Cell Line Aggregates

Single cell recovery and viability was first investigated for Nylon® mesh membranes with 5, 10, 15, 25, or 50 µm pore sizes. To eliminate confounding effects, fabricated devices 10 containing only the first membrane 24 were initially used. This first membrane 24 was used in direct flow mode and not tangential flow mode. Experiments were performed using MCF-7 human breast cancer cells, which are strongly cohesive and provide large numbers of aggregates from standard tissue culture. Note that MCF-7 cells are very large at ~20 µm diameter. Cell suspensions were passed through devices using a syringe pump, and initial tests were performed using direct filtration at 12.5 mL/min. Device effluents were recovered and imaged under phase contract microscopy to identify single cells, clusters of 2 to 3 cells, small aggregates of 4 to 10 cells, and large aggregates of >10 cells. Recovery results for each population are plotted in FIG. 3A. Large and small aggregates constituted 10% and 15% of the control population, respectively. These percentages decreased after filtration, in accordance with pore size, down to <0.5% for the 5 and 10 µm pores. Single cells were initially present at less than 30%, and progressively rose as pore size decreased, reaching a maximum of 85%. Clusters remained around 40-45% for all but the 5 and 10 µm pore sizes, but even then, clusters were still present at a substantial level.

Single cell numbers using a cell counter were quantified, and results are plotted in FIG. 3B after normalization by the control. For the 50 µm pore size, ~15% of single cells were lost, most likely due to holdup or non-specific adhesion within the device 10. For all other pore sizes, more single cells were recovered after filtration, suggesting that a percentage of the aggregate and/or cluster populations were dissociated into single cells. Dissociation became more pronounced as pore size decreased, with single cells increasing by more than 5-fold for the 5 µm pore size. However, extruding cells through smaller pores compromised viability, as determined by flow cytometry using a propidium iodide exclusion assay (FIG. 3C). Specifically, losses in viability scaled inversely with single cell recovery. As a result, the number of viable single cells that were recovered remained constant, around 40% higher than the control, for the 5, 10, and 15 µm pore sizes (see FIGS. 7A-7E).

The effect of flow rate was examined while still utilizing the direct filtration mode. It was found that decreasing flow rate to as low as 0.25 m/min resulted in general trends toward lower single cell numbers and higher viability, but these changes were not significant (FIGS. 3D-3E). Aggregate, cluster, and single cell percentages were also similar for each flow rate (see FIGS. 7A-7E). Finally, tangential filtration mode was investigated by diverting the sample between the cross-flow outlet 18 and effluent outlet 26 using two syringe pumps that were operated in withdrawal mode. The total flow rate was held constant at 12.5 mL/min, similar to direct filtration experiments, while the cross-flow was varied from 40 to 80%. Afterwards, sample collected from the cross-flow outlet was passed through the filter membrane in direct filtration mode at 12.5 mL/min, and both effluents were combined prior to analysis. It was found that single cell numbers were similar at all cross-flow ratios (FIG. 3F), which were significantly lower than direct filtration experiments at 12.5 mL/min (compare to FIG. 3B). In fact, single cell numbers under tangential filtration were similar to direct filtration at 0.25 mL/min, even though all tangential experiments were performed utilized higher membrane flow-through rates (>2.5 mL/min). It was found that tangential filtration removed large aggregates more effectively at the 50 µm pore size (see FIGS. 7A-7E). Taken together, it was concluded that under pressure driven flow, aggregate and cluster dissociation depended primarily on membrane pore size and whether a cross-flow was present, and less so on the flow rate through the membrane.

Improving Aggregate Dissociation Using Two Membranes

Figure 4C:
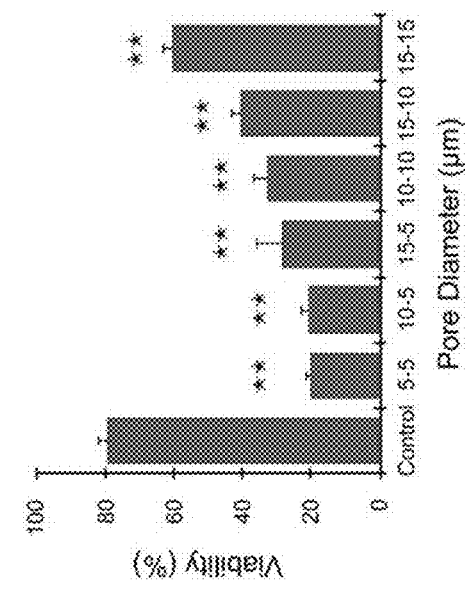
FIG. 4C illustrates a graph of viability percentage as a function of pore diameter. Single cell recovery and viability were generally similar to the single filter, direct filtration experiments for the 5 and 10 μm membranes. The 15-15 membrane device combination did have higher single cell numbers than the 15 μm pore membrane alone.
Figure 4B:
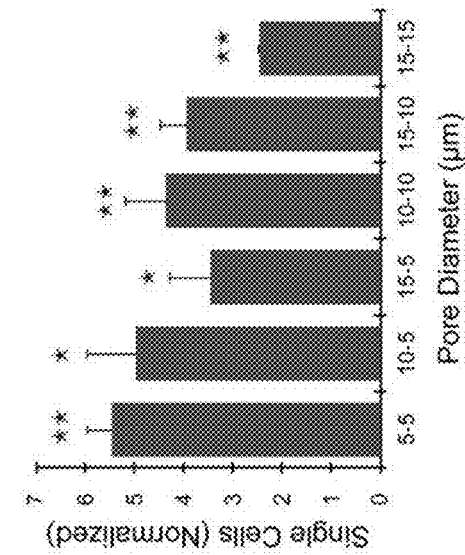
FIG. 4B illustrates a graph of single cells (normalized) (single cell recovery) as a function of pore diameter.
Figure 4A:
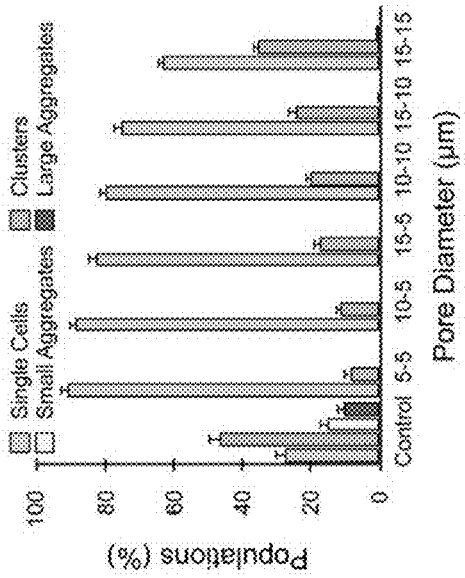
FIG. 4A illustrates a graph of population percentage as a function of pore diameter for various combinations of the 5, 10, and 15 μm membrane filters (combined in series); devices were connected by tubing and operated under direct filtration mode at 12.5 mL/min flow rate. Large and small aggregate populations were eliminated from all filter device combinations.

Based on these results, it was postulated that aggregate dissociation could be enhanced by passing samples through two Nylon® membranes in series. This is because the first membrane would reduce aggregate size such that the second membrane could better liberate single cells. Therefore, two single-membrane filter devices were coupled in series using tubing and performed direct filtration experiments at 12.5 mL/min. Since dissociation was the focus, the smaller pore size membranes were tested in various combinations. It was found that passing MCF-7 suspensions through two filter devices eliminated nearly all aggregates (FIG. 4A), even for the 15 µm pore size. Clusters were also reduced relative to the single filter experiments (compare to FIG. 3A), reaching a low of 9% for the 5-5 membrane combination. Single cell number and viability results are presented in FIG. 4B and FIG. 4C, respectively. Single cell yield did not change for the 5-5 and 10-5 membrane combinations relative to the single filter case (compare to FIG. 3B), as samples were already well-dissociated.

However, the 15-5 membrane combination produced fewer single cells, suggesting that the 15 µm membrane captured aggregates that the 5 µm membrane would have been able to dissociate into single cells. For the 10 µm membrane, single cell numbers were similar between single and double filter device experiments. The only case in which the use of two membranes was beneficial was for the 15-15 membrane combination, which increased single cell numbers increased from 50% to 150% higher than the control. It was found that cell viability was predominantly determined by the pore size of the second, smaller membrane, and that values were similar to the single filter device experiments (compare to FIG. 3C). While it was observed that viability was generally correlated with single cell numbers, live single cell numbers were lowest for conditions that employed the 5 µm membrane (see FIGS. 8A-8F). Thus, the 5 µm pores were deemed too small, at least for these ~20 µm MCF-7 cells. For the 10-10, 15-10, and 15-15 membrane combinations, live single cell recovery was 60% higher than the control. For context, this level of dissociation is comparable to the best version of the branching channel dissociation device for the same MCF-7 cell model.

Figure 4F:
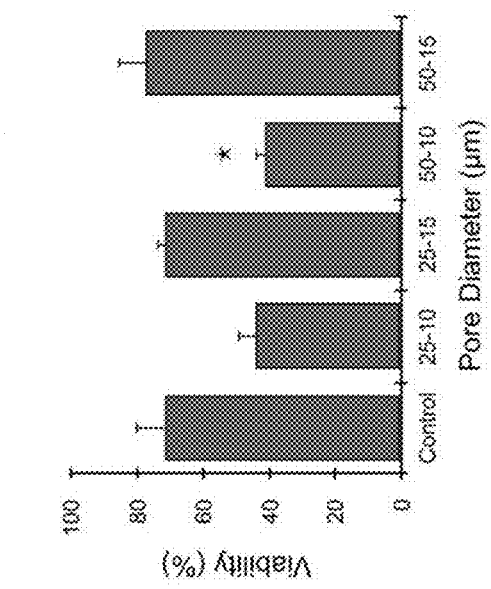
FIGS. 4D-4F illustrate the results of tangential filtration experiments using the 25 or 50 μm membranes followed by the 10 or 15 μm membranes with 60% cross-flow and 12.5 mL/min total flow rate. Results for FIG. 4D show single cell, cluster, and aggregate populations.
Figure 4E:
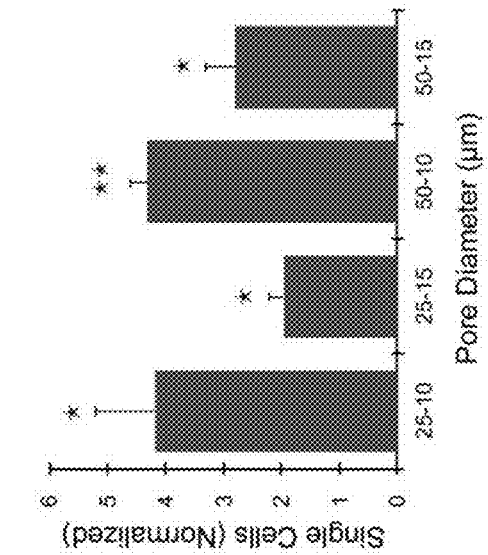
Figure 4D:
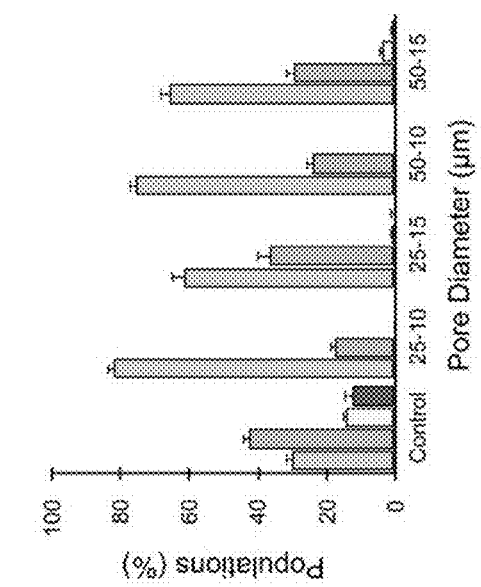

Next, the 10 and 15 µm membranes were investigated in combination with the larger 25 and 50 µm membranes. Two filter devices 10 were coupled in series as previously described, but now experiments were performed under tangential filtration. As with single filter device 10 experiments, total flow rate was held constant at 12.5 mL/min and sample collected from the cross-flow outlet was passed through both devices under direct filtration mode. Using 60% cross-flow, it was found that single cell, cluster, and aggregate populations were similar to the direct flow experiments utilizing the same 10 and 15 µm membranes (FIG. 4D). However, a small number of aggregates were recovered from the 50-15 membrane combination. Single cell recovery and viability results were also generally determined by the second, smaller membrane (FIGS. 4E and 4F). As such, single cell numbers for the 10 µm pore size were similar to direct flow experiments using either one or two filter devices. For the 15 µm pore size, single cell numbers were similar to the 15-15 membrane combination under direct filtration, but now viability was significantly higher and equal to the control. It was unclear whether this change was related to using larger pore sizes in the upstream filter device, tangential filtration mode, or a combination of both. In total, live single cell numbers were 2-fold greater than the control for all but the 25-15 combination (see FIGS. 8A-8F). Note that nearly identical results were obtained for tangential filtration experiments performed using 80% cross-flow (see FIGS. 8A-8F). Based on the combined results obtained with the MCF-7 cell aggregate model, one can conclude that the second membrane predominantly dictated single cell recovery and viability because of its smaller pore size and consistent utilization of the direct filtration mode. Placing a second membrane upstream could improve results in some cases, particularly for the 15 µm membrane, but the pore size and operational mode of the first membrane was less important.

Optimization Using Murine Kidney Tissue

Since the ultimate goal is to use the filter devices with complex tissues, the performance was evaluated using murine kidney tissue samples. The two microfluidic tissue dissociation and filtration devices 10 in series was used, specifically the larger 25 or 50 μm pore sizes followed by smaller 10 or 15 μm pore sizes. The first filtration was performed under direct or tangential (60% cross-flow) mode, and a total flow rate of 12.5 mL/min. Fresh kidneys were harvested, sliced into histologically similar sections with a scalpel, minced into ~1 mm$^3$ pieces, and weighed. Samples were then digested with collagenase and mechanically treated by vortexing and pipetting, per routine protocol. Device performance was initially evaluated using tissue samples that were only briefly digested with collagenase, as this would prove the most stringent test of membrane clogging and dissociation power. After digestion for 15 min, device treatment increased single cell numbers by at least 2-fold for all membrane combinations and filtration modes (FIG. 5A). Maximal results were ~4-fold higher than control, which were obtained for both 25 μm pore size combinations under direct filtration and both 50 μm pore size combinations under tangential filtration. Increasing digestion time to 30 min enhanced single cell recovery for all device conditions, which were now at least 5-fold higher than the control (FIG. 5B). Results were generally greater for the 15 μm pore combinations regardless of the first membrane size or operational mode, which was consistent with the findings with the MCF-7 aggregate model. For both 15 and 30 min digestion times, it was observed that large pieces of tissue were trapped by the first membrane (FIG. 5A), but membrane fouling was not an issue for either direct or tangential filtration modes, most likely because relatively small tissue samples (<100 mg) were used.

Based on these preliminary results, it was decided to further evaluate cell suspensions using flow cytometry. Specifically, a panel of stains were used to assess cell viability and identify red blood cells and leukocytes. Also, only the 50 μm pore size was used in the first device due to higher porosity and the direct filtration mode since it was faster and easier to execute. The number of single tissue cells recovered per mg tissue is shown in FIG. 5C. Results at the 15 and 30 minute digestion times were similar to the cell counter data in FIGS. 5A and 5B, with both 50-10 and 50-15 membrane combinations producing 5- to 10-fold more single cells than the control. Digesting for 60 min resulted in a dramatic increase in single tissue cell numbers to ~20,000/mg. The 50-10 membrane combination was similar to the control, but the 50-15 membrane combination enhanced recovery by 2.5-fold. Notably, the 50-15 membrane combination also produced similar numbers of single tissue cells after digesting for 15 min as the control after digesting for 60 min. Cell viability was ~90% for all conditions at the 15 and 30 minute digestion time points (FIG. 5D). However, 60 min digestion decreased viability to ~80% for the control and ~75% for the 50-15 μm filter combination. Scattering information was also used to quantify the percentage of aggregates relative to single cells (FIG. 5E). Note that samples were passed through a 35 μm cell strainer prior to analysis to prevent clogging of the cytometer, and thus results likely only reflect cell clusters. Aggregate percentage increased progressively with digestion time for controls, from 3 to 11%, indicating that traditional dissociation methods are not effective at reducing tissue all the way down to single cells. Aggregate percentages remained unchanged for the 50-15 membrane combination, but the 50-10 membrane combination reduced aggregates by approximately half at the 30 and 60 minute digestion time points. Red blood cell and leukocyte recoveries are shown in FIGS. 9A-9D, and closely mirrored the single tissue cell recovery results in FIG. 5C.

Filter Device Integration and Validation Using Murine Organ and Tumor Tissues

Figure 6A:
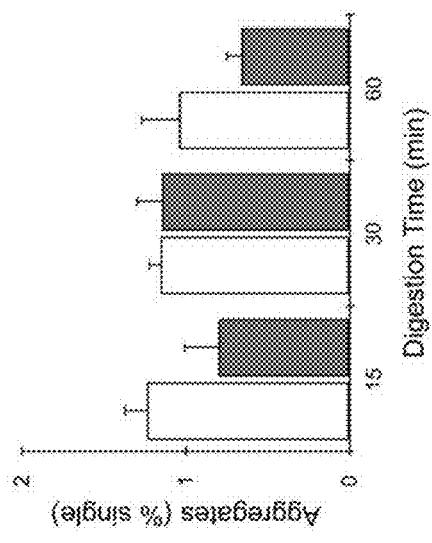
FIGS. 6A-6F illustrate the validation of the integrated dual membrane filter device using murine liver (FIGS. 6A-6C) and mammary tumor tissue samples (FIGS. 6D-6F). Freshly harvested murine liver and breast tumor tissue was minced and digested with collagenase before passing through the microfluidic filter device containing 50 and 15 μm membranes.
Figure 6B:
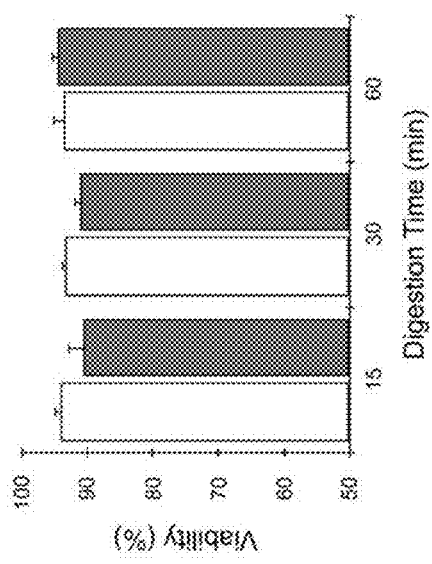
Figure 6C:
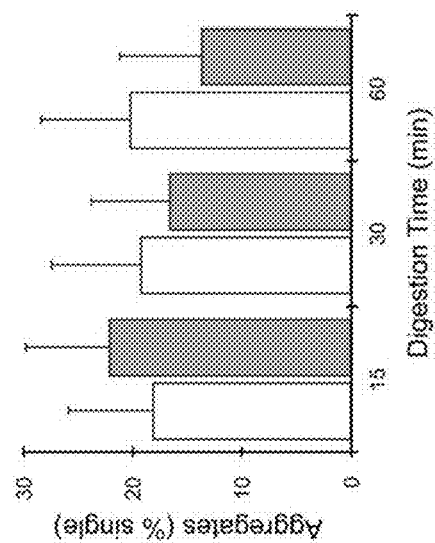
Figure 6D:
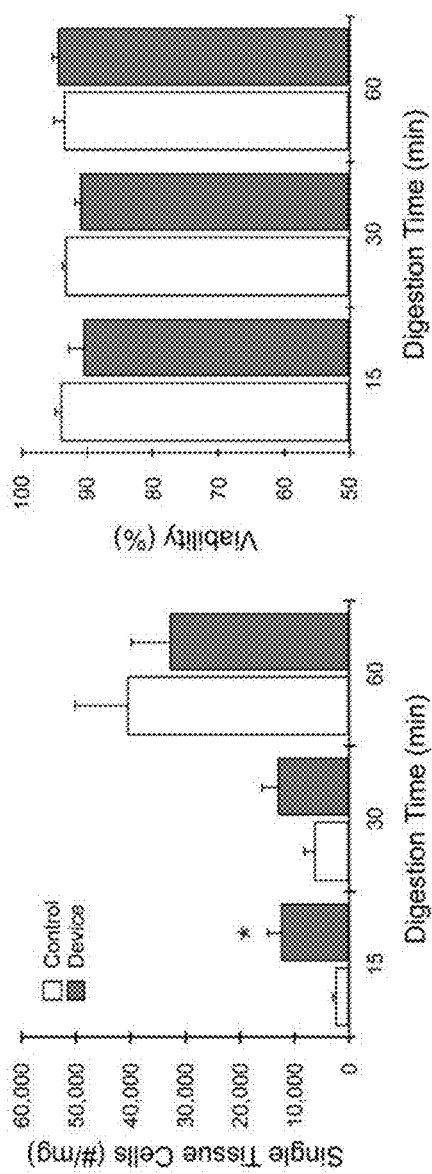
Figure 6E:
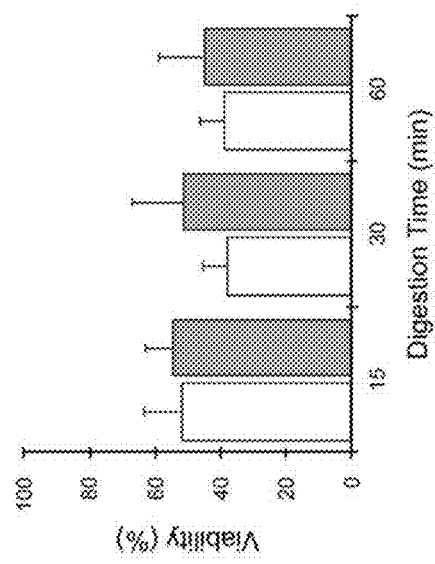
Figure 6F:
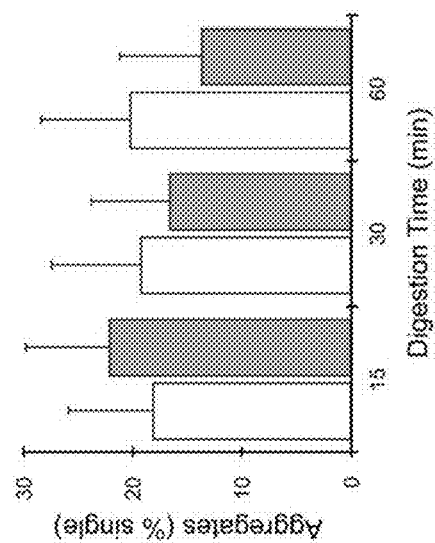
Figure 9A:
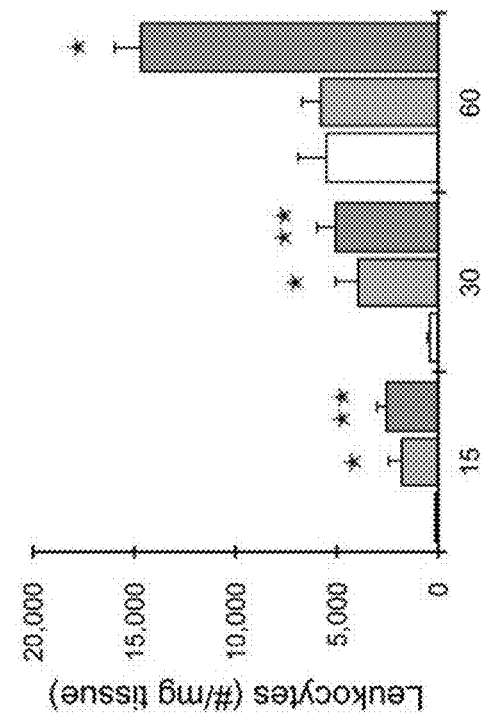
FIGS. 9A-9D illustrates filter device optimization using murine kidney tissue.
Figure 9B:
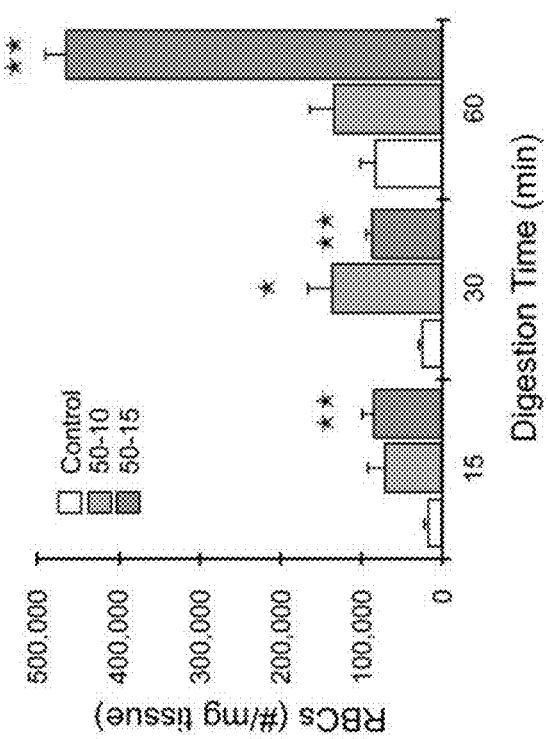
Figure 9C:
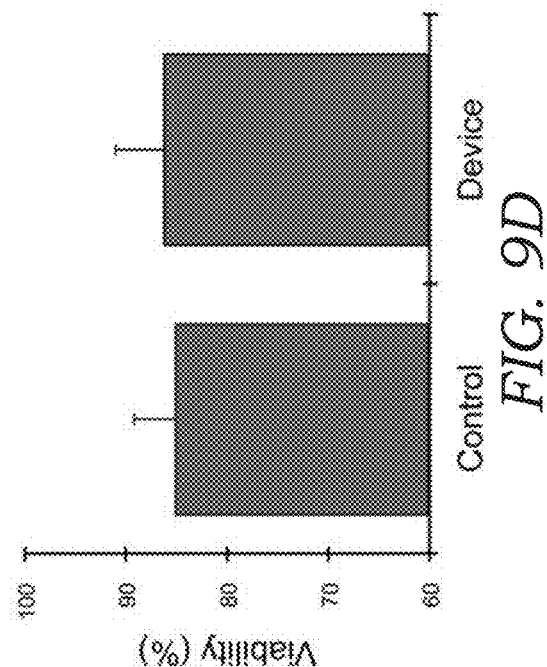
Figure 9D:
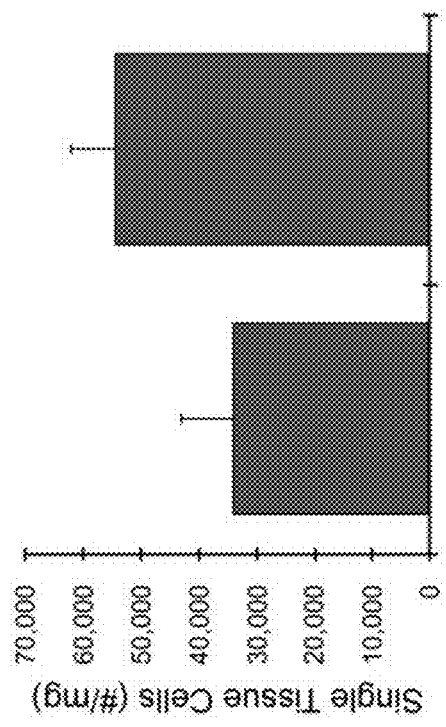
Figure 10B:
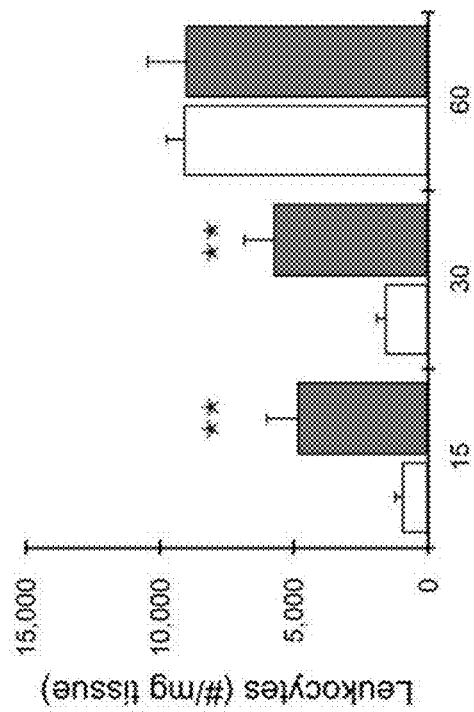
FIGS. 10A-10D illustrates red blood cell and leukocyte recoveries for murine liver and tumor tissue samples. Results are shown for liver (FIGS. 10A, 10B) and mammary tumor cell (FIGS. 10C, 10D) suspensions. Red blood cell and leukocyte cell counts increased with both digestion time and device processing in all cases. Recoveries increased with digestion time and device processing in a manner consistent with single tissue/epithelial cell results in FIGS. 6A-6F. Error bars represent standard errors from at least three independent experiments. * indicates $p<0.05$ and ** indicates $p<0.01$ relative to the control at the same digestion time.
Figure 10D:
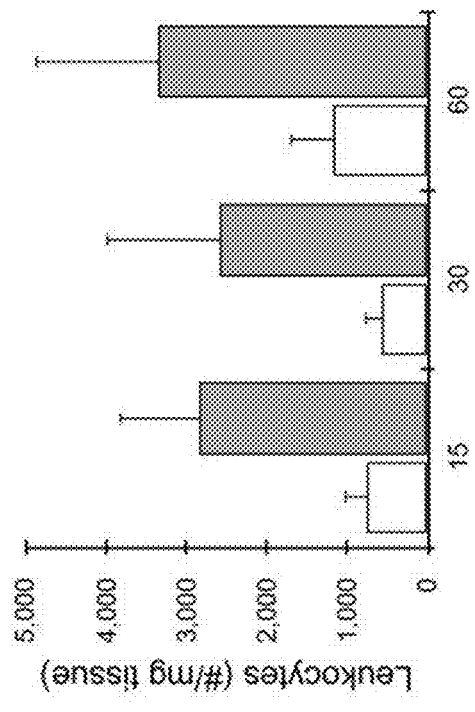
Figure 10A:
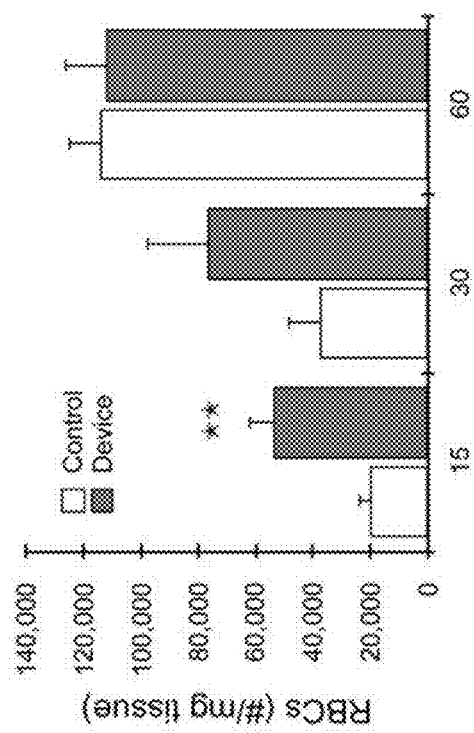
Figure 10C:
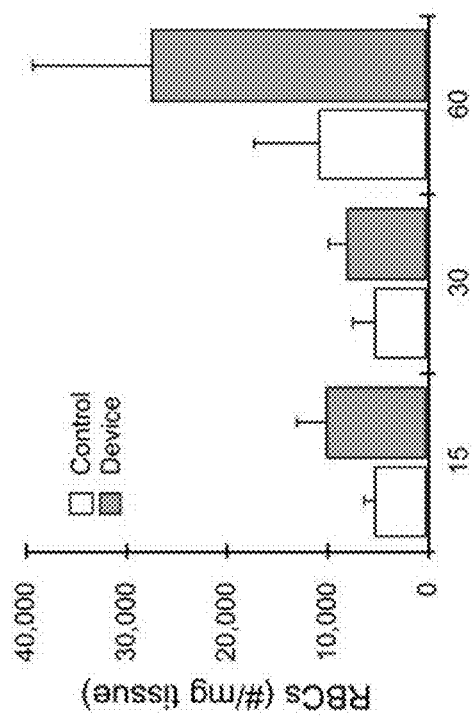

Based on the superior performance of the 50-15 membrane combination in terms of single tissue cells recovered from kidney samples, a single microfluidic tissue dissociation and filtration device 10 was fabricated containing both membranes 24, 28, as shown in FIGS. 1A, 1G, 1H. The double membrane device 10 was first validated using murine kidney samples that were digested for 60 min, and performance in terms of single tissue cell recovery and viability was comparable to the previous results obtained with two single filter devices coupled in series (see FIGS. 9A-9D). Freshly resected murine liver samples were tested, which are generally easier to enzymatically digest, but hepatocytes are also well-known to be fragile. After a brief 15 min digestion, approximately 2,500 single tissue cells were obtained per mg liver tissue for the control, and this was enhanced 5-fold by filter device treatment (FIG. 6A). At 30 min, single tissue cells increased by 2-fold for the control, but device treatment remained static, resulting in a more modest 2-fold improvement. Both control and device conditions were both much higher after 60 min digestion, around 40,000 single tissue cells/mg, indicating that the liver tissue had been fully broken down by enzymatic digestion. Viability remained greater than 90% for all conditions (FIG. 6B), which was very encouraging considering the fragile nature of hepatocytes. Aggregates were present at ~1% for controls at all digestion times, and were generally reduced by device treatment although differences were not significant (FIG. 6C). As a final evaluation, mammary tumors were used that spontaneously arise in MMTV-PyMT transgenic mice. Tumors are generally considered among the most difficult epithelial tissues to dissociate due to their abnormal extracellular matrix composition. For these tests, the flow cytometry detection panel was modified by adding an antibody specific for the general epithelial marker EpCAM. This enabled the positive identification of epithelial tissue cells, although this would include both normal and cancerous cells. Control conditions produced ~1,000 single epithelial cells per mg tumor tissue at both the 15 and 30 min digestion time points, and this only increased to ~2,000 cells/mg after 60 min digestion (FIG. 6D). Device treatment enhanced single cell recovery by approximately 3-fold at all time points. Epithelial cell viability was only ~40-50% for all conditions (FIG. 6E), potentially indicating that the tumor samples contained highly necrotic regions. A significant number of aggregates were present at all conditions, in the range of 15-20% of the total recovered population (FIG. 6F). This suggests that more dissociation power will be needed to effectively liberate all cells from tumors. For both liver and tumor samples, red blood cell and leukocyte recoveries followed similar trends as the single liver tissue cell and single epithelial cell data (see FIGS. 10A-10D).

A new microfluidic tissue dissociation and filtration device 10 is disclosed that is simple and inexpensive, but can also rapidly and effectively improve the quality of single cell suspensions obtained from digested tissue samples. This was accomplished using Nylon® mesh membranes with well-defined, micron-scale pores that simultaneously filtered larger tissue fragments and dissociated smaller aggregates into single cells. Specifically, it was demonstrated that using two Nylon® mesh membranes; a first filter membrane 24 with a larger pore size in the range of 25-50 μm followed by a second filter membrane 28 with a smaller pore size in the range of 10-15 µm, resulted in dissociation of aggregates into progressively smaller sizes and ultimately enhanced single cell recovery. The dissociation effect was likely due to the combination of hydrodynamic shear forces and physical interaction with the Nylon® threads. While this was effective, note that care must be given to prevent cell damage, particularly for complex tissues that may contain cells of different sizes. Using the final dual membrane microfluidic tissue dissociation and filtration device 10 with 50 and 15 µm pore sizes in the respective filter membranes 24, 28, the number of single cells recovered from minced and digested murine kidney, liver, and tumor tissue samples was enhanced by at least 3-fold, and in some cases by more than 10-fold. Moreover, it was shown that a brief 15 min digestion and filter device treatment could produce comparable single cell numbers to a full 60 min digestion, which holds exciting potential to accelerate tissue processing work flows and preserve the natural phenotypic state of cells. Importantly, cell viability was maintained for all tissue types and operating conditions, even for fragile liver cells.

The design also included the option to perform the first filtration (e.g., using filter membrane 24) under tangential mode, although this was not found to be critical for generating single cells. Note that it is possible that tangential filtration could become more important if tissue size were scaled up beyond 100 mg. Also, the microfluidic tissue dissociation and filtration device 10 can be integrated with a hydro-mincing digestion device such as that disclosed in U.S. Patent Application Publication No. 2019/0070605, which is incorporated herein by referenced, to enable automated processing of cm-scale tissue samples. The microfluidic tissue dissociation and filtration device 10 can also be integrated as well with the branching channel dissociation device such as that disclosed in U.S. Pat. No. 9,580,678, which is incorporated herein by reference, to maximize single cell numbers and purity. This integrated platform would be capable of processing full tissue samples all the way down to a highly pure suspension of single cells in a rapid and efficient manner. Furthermore, the microfluidic tissue dissociation and filtration device 10 can be integrated with downstream technologies to enable on-chip sorting and analysis of single cells to create point-of-care diagnostic platforms for tissue samples.

It should also be understood that the invention is not necessarily limited to having two filter membranes 24, 28. In some embodiments, only a single filter membrane 24 may be necessary. In addition, even though the device 10 may have multiple filter membranes (e.g., 24, 28, 32) it may be possible to shunt fluid to avoid one or more of the filter membranes that are located in the device 10. This may be accomplished by plugging or blocking flow in one of the outlets 18, 26, 38. Likewise, other embodiments of microfluidic tissue dissociation and filtration device 10 may have more than two filters such as the embodiment illustrated in FIG. 1C.

Experimental

Device fabrication. Microfluidic devices were fabricated by ALine, Inc. (Rancho Dominguez, CA). Briefly, fluidic channels, vias, and openings for membranes and hose barb were etched into polyethylene terephthalate (PET) layers using a $CO_2$ laser. Nylon® mesh membranes were purchased from Amazon Small Parts (10, 15, 25, and 50 µm pore sizes; Seattle, WA) or EMD Millipore (5 µm; Burlington, MA) as large sheets and were cut to size using the $CO_2$ laser. Device layers, Nylon® mesh membranes, and hose barbs were then assembled, bonded using adhesive, and pressure laminated to form a single monolithic device 10.

Cell culture aggregate model and murine tissue samples. MCF-7 human breast cancer cell line was purchased from ATCC (Manassas, VA). Cells were cultured at 37° C. and 5% $CO_2$ in tissue culture flasks using DMEM media containing 10% FBS, non-essential amino acids, 1 mM sodium pyruvate, 2 mM L-Glutamine, 100 µg/mL streptomycin, 100 U/mL penicillin, and 44 U/L Novolin R insulin (Thermo Fisher, Waltham, MA). Prior to experiments, confluent monolayers were briefly digested for 5 min with trypsin-EDTA, which released cells with a substantial number of aggregates. Cell suspensions were then centrifuged and resuspended in PBS containing 1% BSA (PBS+). Kidneys and liver were harvested from freshly sacrificed BALB/c or C57B/6 mice (Jackson Laboratory, Bar Harbor, ME) that were determined to be waste from a research study approved by the University of California, Irvine's Institutional Animal Care and Use Committee (courtesy of Dr. Angela G. Fleischman). Mammary tumors were harvested from freshly sacrificed MMTV-PyMT mice (Jackson Laboratory, Bar Harbor, ME). For kidneys, a scalpel was used to prepare ~1 cm long x~1 mm diameter strips of tissue, each containing histologically similar portions of the medulla and cortex. Each tissue strip was then further minced with a scalpel to ~1 $mm^3$ pieces. Liver and mammary tumors were uniformly minced with a scalpel to ~1 $mm^3$ pieces. Minced tissue samples were then weighed, placed within microcentrifuge tubes along with 300 µL of 0.25% collagenase type I (Stemcell Technologies, Vancouver, BC), digested at 37° C. in a shaking incubator under gentle agitation for 15, 30, or 60 min, and mechanically disaggregated by repeated pipetting and vortexing. Finally, cell suspensions were treated with 100 Units of DNase I (Roche, Indianapolis, IN) for 10 min at 37° C. and washed by centrifugation into PBS+.

Dissociation and filtration studies. Microfluidic filter devices were prepared by affixing 0.05" ID tubing (Saint-Gobain, Malvern, PA) to the device inlet and outlet hose barbs. Prior to experiments, devices were incubated with SuperBlock (PBS) blocking buffer (Thermo Fisher Scientific, Waltham, MA) at room temperature for 15 min to reduce non-specific binding of cells to the membranes and channel walls and washed with PBS+. MCF-7 cells or digested murine tissue samples were loaded into a syringe and passed through the device using a syringe pump (Harvard Apparatus, Holliston, MA) at total flow rates ranging from 0.25 to 12.5 mL/min. For tangential filtration experiments, two syringe pumps were employed in withdrawal mode, one each connected to the cross-flow and effluent outlets. The withdrawal rates were adjusted to achieve a given cross-flow rate, while total flow rate was always maintained at 12.5 mL/min. Following the initial pass, sample collected from the cross-flow outlet was passed directly through the membrane at 12.5 mL/min and collected from the effluent outlet. Following all experiments, devices were washed with 1 mL PBS+ to flush out any remaining cells, and all effluents were combined into a single sample. Cell counts were obtained using a Moxi Z automated cell counter and type S cassettes (Orflo, Hailey, ID).

Quantifying cell aggregates by microscopy. Single cells and aggregates were assessed by microscopy. Briefly, MCF-7 cell suspensions were imaged with a Hoffman phase contrast microscope and a 4x objective. Raw images were then converted to binary using MATLAB, and ImageJ was used to identify, outline, and calculate the area of all contiguous cellular units. Each unit was then classified based on area as a single cell (20 to 80 pixels$^2$ or 75 to 300 μm$^2$), cluster (80 to 200 pixels$^2$ or 300 to 750 m$^2$), small aggregate (200 to 300 pixels$^2$ or 750 to 1120 m$^2$), or large aggregate (>300 pixels$^2$ or >1120 μm$^2$). Referencing back to the micrographs, this corresponded to ~2 to 3 cells for clusters, ~4-10 cells for small aggregates, and >10 cells for large aggregates.

Flow cytometry. The flow cytometry protocol that was previously developed for tissue suspensions was followed. Briefly, cell suspensions were co-stained with 2.5 μg/mL anti-mouse CD45-PE monoclonal antibody (clone 30-F11, BioLegend, San Diego, CA) and 0.5× CellMask Green (Thermo Fisher, Waltham, MA) for 20 minutes at 37° C. Samples were then washed twice using PBS+ by centrifugation, co-stained with 5 μg/mL 7-AAD (BD Biosciences, San Jose, CA) and 12.5 μM DRAQ5 (BioLegend) on ice for at least 15 minutes, and analyzed on an Accuri C6 Flow Cytometer (BD Biosciences). Flow cytometry data was compensated and analyzed using FlowJo software (FlowJo, Ashland, OR), and a sequential gating scheme was used to identify live and dead single tissue cells from leukocytes, red blood cells, non-cellular debris, and cellular aggregates.

Statistics. Data are represented as the mean standard error. Error bars represent the standard error from at least three independent experiments. P-values were calculated from at least three independent experiments using students t-test.

While embodiments of the present invention have been shown and described, various modifications may be made without departing from the scope of the present invention. For example, the microfluidic tissue dissociation and filtration device 10 has been illustrated as including one, two, or three filter membranes 24, 28, 32. In other embodiments, additional filter membranes may be used (e.g., 4, 5, 6, 7, 8, 9, 10, etc.). Likewise, in another alternative embodiment, the outlet 16 that is used to collect the cross-flow solution (that does not pass directly through the filter membrane) may be turned off or omitted entirely in other embodiments. The invention, therefore, should not be limited, except to the following claims, and their equivalents.

What is claimed is:

1. A microfluidic tissue dissociation and filtration device comprising:
    an inlet coupled to a first microfluidic channel at an upstream location, the first microfluidic channel coupled to a first outlet at a downstream location, wherein the first microfluidic channel is disposed in a first layer of the microfluidic tissue dissociation and filtration device;
    a second microfluidic channel located within a second layer of the microfluidic tissue dissociation and filtration device;
    a first filter membrane interposed between the first microfluidic channel and the second microfluidic channel, wherein the second microfluidic channel is in fluidic communication with the first microfluidic channel by a first connecting fluid passageway containing the first filter membrane;
    a second outlet coupled to a downstream location of the second microfluidic channel;
    a second filter membrane interposed between the second outlet and the second microfluidic channel and contained in a second connecting fluid passageway that fluidically connects the second microfluidic channel to the second outlet;
    a pump connected to a source of tissue or cellular aggregates contained within a fluid, the pump further fluidically connected to the inlet; and
    wherein the first filter membrane comprises pores having diameters of $d_1$ and wherein the second filter membrane comprises pores having diameters of $d_2$, wherein $d_1>d_2$ and wherein the first filter membrane has pore diameters that are at least two times the pore diameters of the second filter membrane, and wherein the second filter membrane is configured to allow passage of single cells and fluid and generates an increase in yield of single cells from the tissue or cell aggregates of at least 3-fold in the second outlet.

2. The microfluidic tissue dissociation and filtration device of claim 1, wherein the first filter membrane has pore diameters greater than 15 μm and less than 1,000 μm and the second filter membrane has pore diameters greater than 5 μm and less than or equal to 100 μm.

3. The microfluidic tissue dissociation and filtration device of claim 2, wherein the first connecting fluid passageway is formed in a third or more additional layers.

4. The microfluidic tissue dissociation and filtration device of claim 1, wherein the first filter membrane and the second filter membrane comprise a single layer of woven mesh polymer thread.

5. The microfluidic tissue dissociation and filtration device of claim 4, wherein the first filter membrane and the second filter membrane are formed from a polyamide thread.

6. The microfluidic tissue dissociation and filtration device of claim 1, wherein the first connecting fluid passageway comprises a via, hole, or aperture that extends between the first microfluidic channel and the second microfluidic channel.

7. The microfluidic tissue dissociation and filtration device of claim 1, wherein the second connecting fluid passageway comprises a via, hole, or aperture that extends between the second microfluidic channel and the second outlet.

8. The microfluidic tissue dissociation and filtration device of claim 1, wherein the first filter membrane and the second filter membrane respectively comprise a single layer of woven mesh that is interposed between the first and second layers of the microfluidic tissue dissociation and filtration device.

9. The microfluidic tissue dissociation and filtration device of claim 1, wherein the pore diameters of the second filter membrane are between 10-20 μm and the first filter membrane has pore diameters that are between 2-3 times larger than the pore diameters of the second filter membrane.

10. The microfluidic tissue dissociation and filtration device of claim 1, wherein the second filter membrane generates an increase in yield of single cells from the tissue or cell aggregates of at least 10-fold in the second outlet.

* * * * *